US008835620B2

(12) United States Patent
Ramanathan et al.

(10) Patent No.: US 8,835,620 B2
(45) Date of Patent: Sep. 16, 2014

(54) VACCINES AGAINST MULTIPLE SUBTYPES OF DENGUE VIRUS

(75) Inventors: Mathura P. Ramanathan, Ardmore, PA (US); Niranjan Sardesai, Blue Bell, PA (US)

(73) Assignee: VGX Pharmaceuticals, LLC, Plymouth Meeting, PA (US)

( * ) Notice: Subject to any disclaimer, the term of this patent is extended or adjusted under 35 U.S.C. 154(b) by 48 days.

(21) Appl. No.: 12/812,268

(22) PCT Filed: Jan. 12, 2009

(86) PCT No.: PCT/US2009/030776

§ 371 (c)(1), (2), (4) Date: Jul. 27, 2010

(87) PCT Pub. No.: WO2009/099716

PCT Pub. Date: Aug. 13, 2009

(65) Prior Publication Data

US 2010/0291144 A1 Nov. 18, 2010

Related U.S. Application Data

(60) Provisional application No. 61/020,490, filed on Jan. 11, 2008.

(51) Int. Cl.

| | |
|---|---|
| ***C07H 21/02*** | (2006.01) |
| ***A61K 39/12*** | (2006.01) |
| ***C07K 14/005*** | (2006.01) |
| *A61K 39/00* | (2006.01) |

(52) U.S. Cl.

CPC ....... *A61K 39/12* (2013.01); *C12N 2770/24134* (2013.01); *C07K 14/005* (2013.01); *C12N 2770/24122* (2013.01); *A61K 2039/53* (2013.01)

USPC .................................... 536/23.72; 424/218.1

(58) Field of Classification Search

None

See application file for complete search history.

(56) References Cited

U.S. PATENT DOCUMENTS

| | | | | |
|---|---|---|---|---|
| 6,165,477 | A | 12/2000 | Ivy | |
| 6,733,994 | B2 * | 5/2004 | Weiner et al. | 435/69.1 |
| 2002/0102729 | A1 * | 8/2002 | MacLaughlin et al. | 435/455 |
| 2004/0009469 | A1 * | 1/2004 | Apt et al. | 435/5 |
| 2005/0163804 | A1 | 7/2005 | Chang | |
| 2007/0041941 | A1 | 2/2007 | Weiner | |

OTHER PUBLICATIONS

Swaminathan et al., Expert Opin. Ther. Patents, 2010, 20(6):819-835.*

Cassetti et al., Vaccine, 2010, 28:4229-4234.*

Nicol et al., Gene Therapy, 2002, 9:1351-1358.*

Crill, et al. Monoclonal Antibodies That Bind to Domain III of Dengue Virus E Glycoprotein Are the Most Efficient Blockers of Virus Absorption to Vero Cells; J. of Virology, Aug. 2001 V.75, No. 16; pp. 7769-7773.

Zhang, Zhishan "The expression of dengue virus type 1 to 4 envelope domain III and its application in serological diagnosis and protective immunity"; Dissertation for Doctors Degree in Fujian Medical University; Mar. 1, 2007; pp. 1-123. Plus a 3 page English Abstract.

Chen, et al. "Induction of Tetravalent Protective Immunity Against Four Dengue Serotypes by the Tandem Domain III of the Envelope Protein"; DNA and Cell Biology, vol. 26, No. 6, 2007; pp. 361-367.

Khanam, et al. "Induction of Neutralizing Antibodies Specific to Dengue Virus Serotypes 2 and 4 by a Bivalent Antigen Composed of Linked Envelope Domains III of These Two Serotypes"; Am. J. Trop Med. Hyg 74(2),2006; pp. 266-277.

Mota, et al. "Induction of protective antibodies against dengue virus by tetravalent DNA immunization of mice with domain III of the envelope protein"; Vaccine, vol. 23, 2005; pp. 3469-3476.

* cited by examiner

*Primary Examiner* — Stacy B. Chen

(74) *Attorney, Agent, or Firm* — Thomas Kim

(57) ABSTRACT

An aspect of the present invention is related to nucleic acid constructs capable of expressing a polypeptide that elicits an immune response in a mammal against more than one subtype of dengue virus, and methods of use thereof. Additionally, there are DNA plasmid vaccines capable of generating in a mammal an immune response against a plurality of dengue virus subtypes, comprising a DNA plasmid and a pharmaceutically acceptable excipient, and methods of use thereof. The DNA plasmid is capable of expressing a consensus dengue antigen in a cell of the mammal in a quantity effective to elicit an immune response in the mammal.

1 Claim, 17 Drawing Sheets

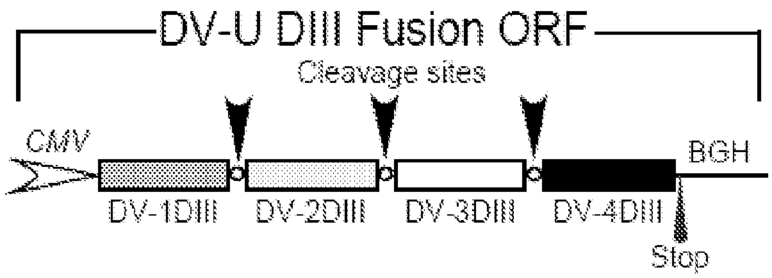

MDWTWILFLVAAATRVHSKGTSYVMCTGSFKLEKEVAETQHGTVLVQ
VKYEGTDAPCKIPFSTQDEKGVTQNGRLITANPIVTDKEKPVNIETE
PPFGESYIVVGAGEKALKLSWFKKGSSIGKMFEATARGARRMAILRG
RKRRSKGMSYSMCTGKFKVVKEIAETQHGTIVIRVQYEGDGSPCKIP
FEIMDLEKRHVLGRLITVNPIVTEKDSPVNIEAEPPFGDSYIIIGVE
PGQLKLNWFKKGSSIGQMFETTMRGAKRMAILRGRKRRSKGMSYAMC
LNTFVLKKEVSETQHGTILIKVEYKGEDAPCKIPFSTEDGQGKAHNG
RLITANPVVTKKEEPVNIEAEPPFGESNIVIGIGDKALKINWYKKGS
SIGKMFEATARGARRMAILRGRKRRSKGMSYTMCSGKFSIDKEMAET
QHGTTVVKVKYEGAGAPCKVPIEIRDVNKEKVVGRIISSTPFAENTN
SVTNIELEPPFGDSYIVIGVGDSALTLHWFRKGSSIGKMFESTYRGA
KRMAIL

FIG. 3

VACCINES AGAINST MULTIPLE SUBTYPES OF DENGUE VIRUS

CROSS-REFERENCE TO RELATED APPLICATIONS

This application is a 371 National stage entry of International Application No. PCT/US2009/030776, filed Jan. 12, 2009, and claims the benefit of U.S. Provisional Application No. 61/020,490, filed Jan. 11, 2008, the contents of which are incorporated herein by reference.

FIELD OF THE INVENTION

The present invention relates to improved dengue vaccines, improved methods for inducing immune responses, and for prophylactically and/or therapeutically immunizing individuals against dengue virus.

BACKGROUND

Dengue virus (DENV) is an emerging mosquito-borne pathogen that causes dengue fever (DF) and severe life threatening illness, dengue hemorrhagic fever/dengue shock syndrome (DHF/DSS). DENV is a small, enveloped, positive-stranded RNA virus that belongs to the Flavivirus genus of the Flaviviridae family. Four distinct subtypes or serotypes of dengue viruses (DV-1 to DV-4) are transmitted to humans through the bites of mosquito species *Aedes aegypti* and *Aedes albopictus*. It has been estimated that 50-100 million cases of DF and 250,000-500000 cases of DHF occur every year. Dengue constitutes a significant international public health concern, as two-fifths of the world's population live in dengue endemic regions, and an estimated 50-100 million cases of dengue infection occur annually. Furthermore 2.5 billion people are at risk for infection in subtropical and tropical regions of the world in the absence of effective intervention.

More than 100 tropical countries have endemic dengue virus infections, and DHF has been documented in >60 of these countries. Surveillance for DF/DHF is poor in most countries, and in the past has focused primarily on DHF; the number of DF cases that occur each year can therefore only be estimated. In 1998, however, major epidemics occurred throughout Asia and the Americas, with >1.2 million cases of DF/DHF reported to the World Health Organization (WHO). Global reports of DHF have increased on average by five-fold in the past 20 years. At the beginning of the 21st century it is estimated that between 50 and 100 million cases of DF and several hundred thousand cases of DHF occur each year, depending on the epidemic activity. The case fatality rate (CFR) varies among countries, but can be as high as 10-15% in some and <1% in others.

There are four dengue virus subtypes: dengue-1 (DV-1), dengue-2 (DV-2), dengue-3 (DV-3), and dengue-4 (DV-4). Each one of these subtypes form an antigenically distinct subgroup within the flavivirus family. They are enveloped, RNA viruses that encode ten proteins: three structural proteins and seven non-structural proteins. The structural proteins are capsid (C), envelope (E) and pre-membrane precursor (preM). The intracellular life cycle of DV begins with receptor-mediated endocytosis of the virus in to cells followed by fusion of the viral envelope protein with the late endosomal membrane, which results in the release of the viral genome into the cytoplasm for replication.

Infection by DV may either be asymptomatic or characterized by fever, chills, frontal headache, myalgia, arthralgia and rash. Subsequent infection with different serotypes may result in more severe manifestations of the disease involving plasma leakage or hemorrhage (dengue hemorrhagic fever) and shock (dengue shock syndrome). Although extensive studies have been carried out over the years to understand the pathogenicity of DENV infection, little progress has been made in the development of specific anti-DV compounds. Currently there are no specific anti viral agents or vaccines against Dengue infections approved in the US.

The envelope (E) glycosylated protein, being the major structural protein present on the surface of the mature dengue virions, is a type I integral membrane protein. It has been demonstrated that the E protein of the mature Dengue forms homodimers in the anti-parallel manner (head to tail orientation). Each monomer is folded into three distinct domains, namely domain I (DI, the central N-terminal domain), domain II (DII, the dimerization domain), and domain III (DIII, immunoglobulin (Ig) like C terminal domain). The DIII domain of E protein consists of 100 amino acids (residues 303-395) of the C-terminus. This domain has been suggested to be the receptor recognition and binding domain. Ig-like fold present in the DIII protein is commonly associated with structures that have an adhesion function. This domain extends perpendicularly to the surface of the virus, with a tip that projects further from the virion surface than any other part of the E protein. In addition, studies have demonstrated that both recombinant DIII proteins and antibodies generated against DIII of E protein of flavivirus can inhibit entry of the flavivirus into target cells. Further, flavivirus with mutation in DIII of the E protein shows either attenuated virulence or the ability to escape immune neutralization.

Development of a safe and effective vaccine against dengue virus infection remains a principal public health goal. Given that the primary correlate of immunity to dengue virus is thought to be the presence of neutralizing antibodies, a prerequisite for comparing and optimizing vaccine candidates is the ability to precisely measure the neutralizing antibody responses evoked by vaccines. A combination of live attenuated virus-containing vaccines from all four serotypes has been shown to result in several complications (Guy B, Almond J W, *Comp Immunol Microbiol Infect Dis*. 2008 March; 31(2-3):239-52). Further, there are few reports on an adenovirus-based delivery of dengue antigens. Nevertheless, the one well recognized problem with adenovirus systems is a majority of the human population is known to have antibodies against one of the adenoviruses, and such pre-existing antibodies can cause these adeno-based vaccines to be ineffective.

Therefore, there remains a need to develop a vaccine that provides broad immunity against multiple and preferably all four serotypes of dengue virus, or universal immunity, and preferably a vaccine which is economical and effective across all serotypes. Further, there remains a need for an effective method of administering vaccines, such as DNA vaccines or DNA plasmid vaccines, to a mammal in order to provide immunization against dengue virus, either prophylatically or therapeutically.

SUMMARY OF THE INVENTION

One aspect of the present invention provides nucleic acid constructs capable of expressing a polypeptide that elicits an immune response in a mammal against more than one subtype of dengue virus. The nucleic acid constructs are comprised of an encoding nucleotide sequence and a promoter operably linked to the encoding nucleotide sequence. The encoding nucleotide sequence expresses the polypeptide, wherein the polypeptide includes domain III of envelope protein (DIII domain or DIII) from at least two different dengue virus subtypes. The promoter regulates expression of the polypeptide in the mammal.

Another aspect of the present invention provides DNA plasmid vaccines that are capable of generating in a mammal an immune response against a plurality of dengue virus subtypes. The DNA plasmid vaccines are comprised of a DNA plasmid capable of expressing a consensus dengue antigen in the mammal and a pharmaceutically acceptable excipient. The DNA plasmid is comprised of a promoter operably linked to a coding sequence that encodes the consensus dengue DIII antigen. The consensus dengue antigen is comprised of consensus DIII domains of dengue virus-subtype 1, dengue virus-subtype 2, dengue virus-subtype 3, or dengue virus-subtype 4

Another aspect of the present invention provides methods of eliciting an immune response against a plurality of subtypes of a virus in a mammal, comprising delivering a DNA plasmid vaccine to tissue of the mammal, the DNA plasmid vaccine comprising a DNA plasmid capable of expressing a plurality of consensus antigens derived from the subtypes of the virus in a cell of the mammal to elicit an immune response in the mammal, the plurality of consensus antigens comprising an antigenic domain from at least two different subtypes of the virus, and electroporating cells of the tissue with a pulse of energy at a constant current effective to permit entry of the DNA plasmids into the cells.

BRIEF DESCRIPTION OF THE DRAWINGS

The numerous objects and advantages of the present invention may be better understood by those skilled in the art by reference to the accompanying figures, in which:

FIG. 3 displays a schematic showing the organization of human codon optimized universal dengue DIII (DV-U) and the consensus amino acid sequence (SEQ ID NO.: 18) of DV-U-DIII.

DETAILED DESCRIPTION OF PREFERRED EMBODIMENTS

Figure 1:
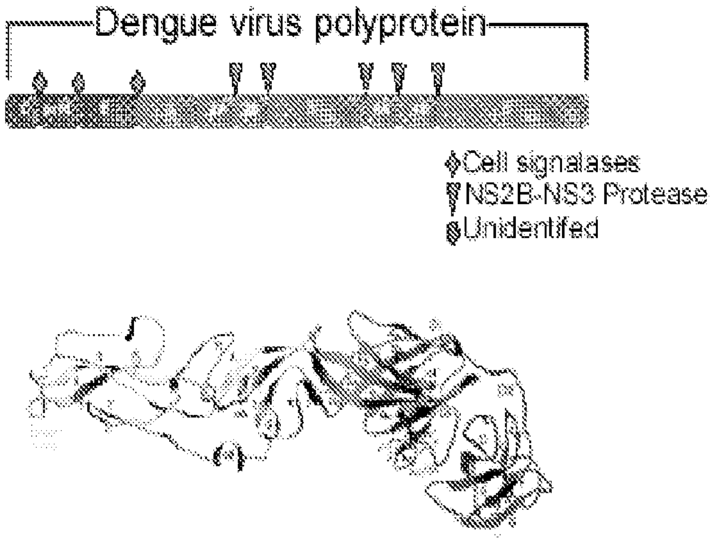
FIG. 1 displays a schematic showing the organization of the dengue virus genome, along with a 3-dimensional conformational model of the dengue virus envelope.
Figure 2:
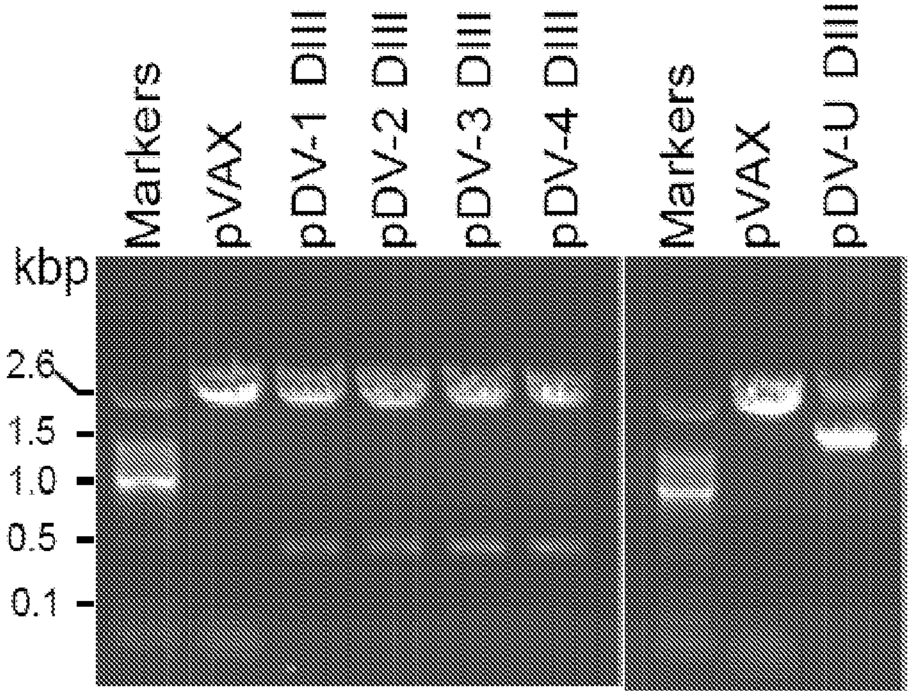
FIG. 2 displays a gel photograph showing the DIII domain from all four dengue subtypes and the universal DIII band.

The following abbreviated, or shortened, definitions are given to help the understanding of the preferred embodiments of the present invention. The abbreviated definitions given here are by no means exhaustive nor are they contradictory to the definitions as understood in the field or dictionary meaning. The abbreviated definitions are given here to supplement or more clearly define the definitions known in the art.

DEFINITIONS

Sequence homology for nucleotides and amino acids as used herein may be determined using FASTA, BLAST and Gapped BLAST (Altschul et al., Nuc. Acids Res., 1997, 25, 3389, which is incorporated herein by reference in its entirety) and PAUP* 4.0b10 software (D. L. Swofford, Sinauer Associates, Massachusetts). Briefly, the BLAST algorithm, which stands for Basic Local Alignment Search Tool is suitable for determining sequence similarity (Altschul et al., J. Mol. Biol., 1990, 215, 403-410, which is incorporated herein by reference in its entirety). Software for performing BLAST analyses is publicly available through the National Center for Biotechnology Information (http://www.ncbi.nlm.nih.gov). One measure of similarity provided by the BLAST algorithm is the smallest sum probability (P(N)), which provides an indication of the probability by which a match between two nucleotide sequences would occur by chance. For example, a nucleic acid is considered similar to another if the smallest sum probability in comparison of the test nucleic acid to the other nucleic acid is less than about 1, preferably less than about 0.1, more preferably less than about 0.01, and most preferably less than about 0.001. "Percentage of similarity" can be calculated using PAUP* 4.0b10 software (D. L. Swofford, Sinauer Associates, Massachusetts). The average similarity of the consensus sequence is calculated compared to all sequences in the phylogenic tree.

As used herein, the term "nucleic acid construct" refers to the DNA or RNA molecules that comprise a nucleotide sequence that encodes protein. The coding sequence, or "encoding nucleic acid sequence," can include initiation and termination signals operably linked to regulatory elements including a promoter and polyadenylation signal capable of directing expression in the cells of the individual to whom the nucleic acid molecule is administered.

As used herein, the term "expressible form" refers to nucleic acid constructs that contain the necessary regulatory elements operably linked to a coding sequence that encodes a protein such that when present in the cell of the individual, the coding sequence will be expressed.

The term "constant current" is used herein to define a current that is received or experienced by a tissue, or cells defining said tissue, over the duration of an electrical pulse delivered to same tissue. The electrical pulse is delivered from the electroporation devices described herein. This current remains at a constant amperage in said tissue over the life of an electrical pulse because the electroporation device provided herein has a feedback element, preferably having instantaneous feedback. The feedback element can measure the resistance of the tissue (or cells) throughout the duration of the pulse and cause the electroporation device to alter its electrical energy output (e.g., increase voltage) so current in same tissue remains constant throughout the electrical pulse (on the order of microseconds), and from pulse to pulse. In some embodiments, the feedback element comprises a controller.

The term "feedback" or "current feedback" is used interchangeably and means the active response of the provided electroporation devices, which comprises measuring the current in tissue between electrodes and altering the energy output delivered by the EP device accordingly in order to maintain the current at a constant level. This constant level is preset by a user prior to initiation of a pulse sequence or electrical treatment. Preferably, the feedback is accomplished by the electroporation component, e.g., controller, of the electroporation device, as the electrical circuit therein is able to continuously monitor the current in tissue between electrodes and compare that monitored current (or current within tissue) to a preset current and continuously make energy-output adjustments to maintain the monitored current at preset levels. In some embodiments, the feedback loop is instantaneous as it is an analog closed-loop feedback.

The terms "electroporation," "electro-permeabilization," or "electro-kinetic enhancement" ("EP"), as used interchangeably herein, refer to the use of a transmembrane electric field pulse to induce microscopic pathways (pores) in a bio-membrane; their presence allows biomolecules such as plasmids, oligonucleotides, siRNA, drugs, ions, and/or water to pass from one side of the cellular membrane to the other.

The term "decentralized current" is used herein to define the pattern of electrical currents delivered from the various needle electrode arrays of the electroporation devices described herein, wherein the patterns minimize, or preferably eliminate, the occurrence of electroporation related heat stress on any area of tissue being electroporated.

The term "feedback mechanism" as used herein refers to a process performed by either software or hardware (or firmware), which process receives and compares the impedance of the desired tissue (before, during, and/or after the delivery of pulse of energy) with a present value, preferably current, and adjusts the pulse of energy delivered to achieve the preset value. The term "impedance" is used herein when discussing the feedback mechanism and can be converted to a current value according to Ohm's law, thus enabling comparisons with the preset current. In a preferred embodiment, the "feedback mechanism" is performed by an analog closed loop circuit.

The term "immune response" is used herein to mean the activation of a host's immune system, e.g., that of a mammal, in response to the introduction of a dengue antigen, e.g., universal dengue antigen, via the provided DNA plasmid vaccines. The immune response can be in the form of a cellular or humoral response, or both.

The term "consensus" or "consensus sequence" is used herein to mean a synthetic nucleic acid sequence, or corresponding polypeptide sequence, constructed based on analysis of an alignment of multiple strains of a specific dengue subtype, which yields the consensus dengue DIII sequences of subtype-1, subtype-2, subtype-3, subtype-4, and the universal dengue described below. The consensus universal dengue can be used to induce broad immunity against multiple subtypes or serotypes of dengue virus.

The term "adjuvant" is used herein to mean any molecule added to the DNA plasmid vaccines described herein to enhance antigenicity of the dengue antigen encoded by the DNA plasmids and encoding nucleic acid sequences described hereinafter.

The term "subtype" or "serotype" is used herein interchangeably and in reference to a virus, for example dengue virus, and means genetic variants of that virus antigen such that one subtype is recognized by an immune system apart from a different subtype. For example, dengue virus subtype 1 is immunologically distinguishable from dengue virus subtype 2.

One aspect of the present invention provides nucleic acid constructs capable of expressing a polypeptide that elicits an immune response in a mammal against more than one subtype of dengue virus. The nucleic acid constructs are comprised of an encoding nucleotide sequence and a promoter operably linked to the encoding nucleotide sequence. The encoding nucleotide sequence expresses the polypeptide, wherein the polypeptide includes a DIII domain from at least two different dengue virus subtypes. The promoter regulates expression of the polypeptide in the mammal.

In some embodiments the nucleic acid construct can further include an IgE leader sequence operatively linked to an N-terminal end of the coding sequence and operably linked to the promoter. Preferably, the IgE leader has the sequence of SEQ ID NO: 11. The nucleic acid construct can also comprise a polyadenylation sequence attached to the C-terminal end of the coding sequence. Preferably, the nucleic acid construct is codon optimized.

In some embodiments, the encoding nucleotide sequence encodes a polypeptide that includes DIII domain from Dengue virus-subtype 1, Dengue virus-subtype 2, Dengue virus-subtype 3, and Dengue virus-subtype 4. In preferred embodiments, the encoding nucleotide sequence is selected from the group consisting of SEQ ID NO:1, SEQ ID NO:2, SEQ ID NO:3, SEQ ID NO:4, and SEQ ID NO:5.

In some embodiments, the encoding nucleotide sequences are a part of an expression cassette and can include the following nucleotide sequences: SEQ ID NO: 12, SEQ ID NO: 13, SEQ ID NO: 14, SEQ ID NO: 15, and SEQ ID NO: 16. The expression cassettes include (from 5' end to 3' end): a KpnI site, IgE leader, encoding sequence (DIII), two stop codons, and a PstI site. One of ordinary skill, equipped with available art, can alter the cassette by replacing either splice site (KpnI or PstI) with alternate splice sites, IgE leader sequence with alternate signaling or targeting leader sequence, and/or stop codons with more or less stop codons.

Another aspect of the present invention provides DNA plasmid vaccines that are capable of generating in a mammal an immune response against a plurality of dengue virus subtypes. The DNA plasmid vaccines are comprised of a DNA plasmid capable of expressing a consensus dengue antigen in the mammal and a pharmaceutically acceptable excipient. The DNA plasmid is comprised of a promoter operably linked to a coding sequence that encodes the consensus dengue antigen. The consensus dengue antigen is comprised of consensus DIII domains of dengue virus-subtype 1, dengue virus-subtype 2, dengue virus-subtype 3, or dengue virus-subtype 4. Preferably, the DNA plasmid comprises a consensus dengue antigen that encodes a consensus DIII domain selected from the group consisting of: SEQ ID NO: 6, SEQ ID NO: 7, SEQ ID NO: 8, SEQ ID NO: 9, and SEQ ID NO: 10. The consensus DIII domain DV-U-DIII that has the sequence SEQ ID NO: 10 consists of linker sequences connecting each of the four subtypes of DIII (DV-1-DIII, DV-2-DIII, DV-3-DIII, and DV-4-DIII), which has the sequence RGRKRRS SEQ ID NO: 17 which is a known cleavage site and allows cleavage of DV-U-DIII into separate DIII sequences of a specific subtype. However, the linker sequence can be any other linker sequence available in the art that has similar characteristics; and it is within the ordinary skill in the art to replace such linker for RGRKRRS SEQ ID NO: 17 currently utilized.

In some embodiments, the DNA plasmid further comprises an IgE leader sequence attached to an N-terminal end of the coding sequence and operably linked to the promoter. Preferably, the IgE leader has the sequence of SEQ ID NO: 11. The DNA plasmid can further include a polyadenylation sequence attached to the C-terminal end of the coding sequence. Preferably, the DNA plasmid is codon optimized.

In some embodiments, the pharmaceutically acceptable excipient is an adjuvant. Preferably, the adjuvant is selected from the group consisting of: IL-12 and IL-15. In some embodiments, the pharmaceutically acceptable excipient is a transfection facilitating agent. Preferably, the transfection facilitating agent is a polyanion, polycation, or lipid, and more preferably poly-L-glutamate. Preferably, the poly-L-glutamate is at a concentration less than 6 mg/ml. Preferably, the DNA plasmid vaccine has a concentration of total DNA plasmid of 1 mg/ml or greater.

In some embodiments, the DNA plasmid comprises a plurality of unique DNA plasmids, wherein each of the plurality of unique DNA plasmids encodes a polypeptide comprising a DIII domain from dengue virus-subtype 1, dengue virus-subtype 2, dengue virus-subtype 3, or dengue virus-subtype 4.

The DNA plasmid vaccines can include a DNA plasmid comprising encoding nucleotide sequences: SEQ ID NO: 1, SEQ ID NO:2, SEQ ID NO:3, SEQ ID NO:4, or SEQ ID NO:5, and preferably SEQ ID NO: 5. In some embodiments the DNA plasmid comprises at least two of the encoding nucleotide sequences: SEQ ID NO: 1, SEQ ID NO: 2, SEQ ID NO: 3, or SEQ ID NO: 4. In some embodiments the DNA plasmid comprises SEQ ID NO: 1 and SEQ ID NO: 2; in some embodiments the DNA plasmid comprises SEQ ID NO: 1 and SEQ ID NO: 3; in some embodiments the DNA plasmid comprises SEQ ID NO: 1 and SEQ ID NO: 4; in some embodiments the DNA plasmid comprises SEQ ID NO: 2 and SEQ ID NO: 3; in some embodiments the DNA plasmid comprises SEQ ID NO: 2 and SEQ ID NO: 4; in some embodiments the DNA plasmid comprises SEQ ID NO: 3 and SEQ ID NO: 4; in some embodiments the DNA plasmid comprises SEQ ID NO: 1, SEQ ID NO: 2 and SEQ ID NO: 3; in some embodiments the DNA plasmid comprises SEQ ID NO: 1, SEQ ID NO: 2 and SEQ ID NO: 4; in some embodiments the DNA plasmid comprises SEQ ID NO: 1, SEQ ID NO: 3 and SEQ ID NO: 3; in some embodiments the DNA plasmid comprises SEQ ID NO: 2, SEQ ID NO: 3 and SEQ ID NO: 4; or in some embodiments the DNA plasmid comprises SEQ ID NO: 1, SEQ ID NO: 2, SEQ ID NO: 3 and SEQ ID NO: 4. Preferably, the DNA plasmid comprises SEQ ID NO: 1, SEQ ID NO: 2, SEQ ID NO: 3, and SEQ ID NO: 4.

In some embodiments, the DNA plasmid vaccines comprises at least two different DNA plasmids that express a dengue virus DIII domain, the plasmids selected from the group consisting of: a DNA plasmid comprising a sequence that encodes a consensus dengue virus-subtype 1 DIII domain, a DNA plasmid comprising a sequence that encodes a consensus dengue virus-subtype 2 DIII domain, a DNA plasmid comprising a sequence that encodes a consensus dengue virus-subtype 3 DIII domain, and a DNA plasmid comprising a sequence that encodes a consensus dengue virus-subtype 4 DIII domain. In some embodiments, the DNA plasmid vaccines can include four consensus dengue virus subtype DIII domains (subtypes 1-4).

In some embodiments, the consensus dengue virus-subtype 1 DIII domain has a nucleic acid sequence comprising SEQ ID NO: 1. In some embodiments, the consensus dengue virus-subtype 2 DIII domain has a nucleic acid sequence comprising SEQ ID NO: 2. In some embodiments, the consensus dengue virus-subtype 3 DIII domain has a nucleic acid sequence comprising SEQ ID NO: 3. In some embodiments, the consensus dengue virus-subtype 4 DIII domain has a nucleic acid sequence comprising SEQ ID NO: 4.

In some embodiments, the mammal in which the DNA plasmid vaccines generate an immune response is a primate. Preferably, the mammal is a primate. The immune response can be either a humoral response or cellular response, and preferably both.

Another aspect of the present invention provides methods of eliciting an immune response against a plurality of dengue virus subtypes in a mammal, comprising delivering a DNA plasmid vaccine to tissue of the mammal and electroporating cells of the tissue with a pulse of energy at a constant current effective to permit entry of the DNA plasmids into the cells.

In some embodiments, the methods of eliciting an immune response includes a delivering step that comprises injecting the DNA plasmid vaccine into intradermic, subcutaneous or muscle tissue.

In some embodiments, the methods of eliciting an immune response can further comprise presetting a current that is desired to be delivered to the tissue; and electroporating cells of the tissue with a pulse of energy at a constant current that equals the preset current.

In some embodiments, the methods of eliciting an immune response further comprise measuring the impedance in the electroporated cells; adjusting energy level of the pulse of energy relative to the measured impedance to maintain a constant current in the electroporated cells. The measuring and adjusting steps preferably occur within a lifetime of the pulse of energy.

In some embodiments, the electroporating step comprises delivering the pulse of energy to a plurality of electrodes according to a pulse sequence pattern that delivers the pulse of energy in a decentralized pattern.

In some embodiments of the present invention, the DNA plasmid vaccines can further include an adjuvant. In some embodiments, the adjuvant is selected from the group consisting of: alpha-interferon, gamma-interferon, platelet derived growth factor (PDGF), TNFα, TNFβ, GM-CSF, epidermal growth factor (EGF), cutaneous T cell-attracting chemokine (CTACK), epithelial thymus-expressed chemokine (TECK), mucosae-associated epithelial chemokine (MEC), IL-12, IL-15, MHC, CD80, CD86 including IL-15 having the signal sequence deleted and optionally including the signal peptide from IgE. Other genes which may be useful adjuvants include those encoding: MCP-1, MIP-1-alpha, MIP-1p, IL-8, RANTES, L-selectin, P-selectin, E-selectin, CD34, GlyCAM-1, MadCAM-1, LFA-1, VLA-1, Mac-1, pl50.95, PECAM, ICAM-1, ICAM-2, ICAM-3, CD2, LFA-3, M-CSF, G-CSF, IL-4, mutant forms of IL-18, CD40, CD40L, vascular growth factor, fibroblast growth factor, IL-7, nerve growth factor, vascular endothelial growth factor, Fas, TNF receptor, Flt, Apo-1, p55, WSL-1, DR3, TRAMP, Apo-3, AIR, LARD, NGRF, DR4, DR5, KILLER, TRAIL-R2, TRICK2, DR6, Caspase ICE, Fos, c-jun, Sp-1, Ap-1, Ap-2, p38, p65Reli, MyD88, IRAK, TRAF6, IkB, Inactive NIK, SAP K, SAP-1, JNK, interferon response genes, NFkB, Bax, TRAIL, TRAILrec, TRAILrecDRC5, TRAIL-R3, TRAIL-R4, RANK, RANK LIGAND, Ox40, Ox40 LIGAND, NKG2D, MICA, MICB, NKG2A, NKG2B, NKG2C, NKG2E, NKG2F, TAP1, TAP2 and functional fragments thereof. In some preferred embodiments, the adjuvant is selected from IL-12, IL-15, CTACK, TECK, or MEC.

In some embodiments, the pharmaceutically acceptable excipient is a transfection facilitating agent, which can include the following: surface active agents, such as immune-stimulating complexes (ISCOMS), Freunds incomplete adjuvant, LPS analog including monophosphoryl lipid A, muramyl peptides, quinone analogs, vesicles such as squalene and squalene, hyaluronic acid, lipids, liposomes, calcium ions, viral proteins, polyanions, polycations, or nanoparticles, or other known transfection facilitating agents. Preferably, the transfection facilitating agent is a polyanion, polycation, including poly-L-glutamate (LGS), or lipid. Preferably, the transfection facilitating agent is poly-L-glutamate, and more preferably, the poly-L-glutamate is present in the DNA plasmid vaccine at a concentration less than 6 mg/ml. In some embodiments, the concentration of poly-L-glutamate in the DNA plasmid vaccine is less than 4 mg/ml, less than 2 mg/ml, less than 1 mg/ml, less than 0.750 mg/ml, less than 0.500 mg/ml, less than 0.250 mg/ml, less than 0.100 mg/ml, less than 0.050 mg/ml, or less than 0.010 mg/ml.

In some embodiments, the DNA plasmid vaccine can be delivered to a mammal to elicit an immune response; preferably the mammal is a primate, including human and nonhuman primate, a cow, pig, chicken, dog, or ferret. More preferably, the mammal is a human primate.

One aspect of the present invention relates to methods of eliciting an immune response against a plurality of subtypes of a virus in a mammal. The methods include delivering a DNA plasmid vaccine to tissue of the mammal, and electroporating cells of the tissue with a pulse of energy at a constant current effective to permit entry of the DNA plasmids into the cells. The DNA plasmid vaccine comprises a DNA plasmid capable of expressing a plurality of consensus antigens derived from the subtypes of the virus in a cell of the mammal to elicit an immune response in the mammal, the plurality of consensus antigens comprising an antigenic domain from at least two different subtypes of the virus. The virus can be selected from one of a number of virus that are known to have distinct serotypes and preferably the virus will have an antigenic domain that is highly conserved across the different serotypes. Preferably, the virus is selected from west nile virus, human immunodeficiency virus, influenza virus, or dengue virus.

One aspect of the present invention relates to methods of eliciting an immune response against a plurality of dengue virus subtypes in a mammal. The methods include delivering a DNA plasmid vaccine to tissue of the mammal, the DNA plasmid vaccine comprising a DNA plasmid capable of expressing a consensus dengue antigen in a cell of the mammal to elicit an immune response in the mammal, the consensus dengue antigen comprising consensus sequences coding for domain III of Envelope protein from at least two dengue subtypes, and preferably all four dengue subtypes. The dengue subtypes include subtype-1, subtype-2, subtype-3, and subtype-4. The methods of eliciting an immune response including electroporating cells of the tissue with a pulse of energy at a constant current effective to permit entry of the DNA plasmids in the cells.

In some embodiments, the methods of the present invention include the delivering step, which comprises injecting the DNA plasmid vaccine into intradermic, subcutaneous or muscle tissue. Preferably, these methods include using an in vivo electroporation device to preset a current that is desired to be delivered to the tissue; and electroporating cells of the tissue with a pulse of energy at a constant current that equals the preset current. In some embodiments, the electroporating step further comprises: measuring the impedance in the electroporated cells; adjusting energy level of the pulse of energy relative to the measured impedance to maintain a constant current in the electroporated cells; wherein the measuring and adjusting steps occur within a lifetime of the pulse of energy.

In some embodiments, the electroporating step comprises delivering the pulse of energy to a plurality of electrodes according to a pulse sequence pattern that delivers the pulse of energy in a decentralized pattern.

The present invention also comprises DNA fragments that encode a polypeptide capable of eliciting an immune response in a mammal substantially similar to that of the non-fragment for at least one dengue virus subtype. The DNA fragments are fragments selected from at least one of the various encoding nucleotide sequences of the present invention, including SEQ ID NOS:1, 2, 3, 4, and 5, and can be any of the following described DNA fragments, as it applies to the specific encoding nucleic acid sequence provided herein. In some embodiments, DNA fragments can comprise 30 or more, 45 or more, 60 or more, 75 or more, 90 or more, 120 or more, 150 or more, 180 or more, 210 or more, 240 or more, 270 or more, 300 or more, 320 or more, 340 or more, or 360 or more nucleotides. In some embodiments, DNA fragments can comprise coding sequences for the immunoglobulin E (IgE) leader sequences. In some embodiments, DNA fragments can comprise fewer than 60, fewer than 75, fewer than 90, fewer than 120, fewer than 150, fewer than 180, fewer than 210, fewer than 240, fewer than 270, fewer than 300, fewer than 320, fewer than 340, or fewer than 360 nucleotides. Preferably, the DNA fragments are fragments of SEQ ID NOS:1, 2, 3, 4, or 5, and more preferably fragments of SEQ ID NOS:1, 2, 3, or 4.

The present invention includes polypeptides encoded by the encoding nucleotide sequences and can include polypeptides having amino acid sequences of SEQ ID NOS: 6, 7, 8, 9, or 10. The present invention also comprises polypeptide fragments that are capable of eliciting an immune response in a mammal substantially similar to that of the non-fragment for at least one dengue subtype. The polypeptide fragments are selected from at least one of the various polypeptide sequences of the present invention, including SEQ ID NOS: 5, 6, 7, 8, 9, and 10, and can be any of the following described polypeptide fragments, as it applies to the specific polypeptide sequence provided herein. In some embodiments, polypeptide fragments can comprise 15 or more, 30 or more, 45 or more, 60 or more, 75 or more, 90 or more, 100 or more, 110 or more, or 120 or more amino acids. In some embodiments, polypeptide fragments can comprise fewer than 30, fewer than 45, fewer than 60, fewer than 75, fewer than 90, fewer than 100, fewer than 110, or fewer than 120 amino acids. Preferably, the polypeptide fragments are fragments of SEQ ID NOS: 5, 6, 7, 8, 9, or 10, and more preferably fragments of SEQ ID NOS: 5, 6, 7, 8, or 9.

The determination of a functional fragment eliciting an immune response in a mammal substantially similar to that of the non-fragment for at least one dengue subtype can be readily determined by one of ordinary skill. The fragment can be analyzed to contain at least one, preferably more, antigenic epitopes as provided by a publicly available database, such as National Center for Biotechnology Information (NCBI). In addition, immune response studies can be routinely assessed using mice and antibody titers and ELISpots analysis, such as that shown in the Examples below.

Vaccines

In some embodiments, the invention provides improved vaccines by providing proteins and genetic constructs that encode proteins with epitopes that make them particularly effective as immunogens against which immune responses can be induced. Accordingly, vaccines can be provided to induce a therapeutic or prophylactic immune response.

According to some embodiments of the invention, a vaccine according to the invention is delivered to an individual to modulate the activity of the individual's immune system and thereby enhance the immune response. When a nucleic acid molecule that encodes the protein is taken up by cells of the individual the nucleotide sequence is expressed in the cells and the protein is thereby delivered to the individual. Aspects of the invention provide methods of delivering the coding sequences of the protein on nucleic acid molecule such as plasmid.

According to some aspects of the present invention, compositions and methods are provided which prophylactically and/or therapeutically immunize an individual.

When taken up by a cell, the DNA plasmids can remain in the cell as separate genetic material. Alternatively, RNA may be administered to the cell. It is also contemplated to provide the genetic construct as a linear minichromosome including a centromere, telomeres and an origin of replication. Genetic constructs include regulatory elements necessary for gene expression of a nucleic acid molecule. The elements include: a promoter, an initiation codon, a stop codon, and a polyadenylation signal. In addition, enhancers are often required for gene expression of the sequence that encodes the target protein or the immunomodulating protein. It is necessary that these elements be operable linked to the sequence that encodes the desired proteins and that the regulatory elements are operably in the individual to whom they are administered.

Initiation codons and stop codon are generally considered to be part of a nucleotide sequence that encodes the desired protein. However, it is necessary that these elements are functional in the mammals to whom the nucleic acid construct is administered. The initiation and termination codons must be in frame with the coding sequence.

Promoters and polyadenylation signals used must be functional within the cells of the individual.

Examples of promoters useful to practice the present invention, especially in the production of a genetic vaccine for humans, include but are not limited to promoters from simian virus 40 (SV40), mouse mammary tumor virus (MMTV) promoter, human immunodeficiency virus (HIV) such as the bovine immunodeficiency virus (BIV) long terminal repeat (LTR) promoter, Moloney virus, avian leukosis virus (ALV), cytomegalovirus (CMV) such as the CMV immediate early promoter, Epstein Barr virus (EBV), Rous sarcoma virus (RSV) as well as promoters from human genes such as human actin, human myosin, human hemoglobin, human muscle creatine and human metalothionein; in other embodiments, promoters can be tissue specific promoters, such as muscle or skin specific promoters, natural or synthetic. Examples of such promoters are described in US patent application publication no. US20040175727, which is incorporated hereby in its entirety.

Examples of polyadenylation signals useful to practice the present invention, especially in the production of a genetic vaccine for humans, include but are not limited to SV40 polyadenylation signals, LTR polyadenylation signals, bovine growth hormone (bGH) polyadenylation signals, human growth hormone (hGH) polyadenylation signals, and human β-globin polyadenylation signals. In particular, the SV40 polyadenylation signal that is in pCEP4 plasmid (Invitrogen, San Diego, Calif.), referred to as the SV40 polyadenylation signal, can be used.

In addition to the regulatory elements required for DNA expression, other elements may also be included in the DNA molecule. Such additional elements include enhancers. The enhancer may be selected from the group including but not limited to: human actin, human myosin, human hemoglobin, human muscle creatine and viral enhancers such as those from CMV, RSV and EBV.

Genetic constructs can be provided with mammalian origin of replication in order to maintain the construct extrachromosomally and produce multiple copies of the construct in the cell. Plasmids pVAX1, pCEP4 and pREP4 from Invitrogen (San Diego, Calif.) contain the Epstein Barr virus origin of replication and nuclear antigen EBNA-1 coding region which produces high copy episomal replication without integration.

In order to maximize protein production, regulatory sequences may be selected which are well suited for gene expression in the cells the construct is administered into. Moreover, codons that encode said protein may be selected which are most efficiently transcribed in the host cell. One having ordinary skill in the art can produce DNA constructs that are functional in the cells.

In some embodiments, nucleic acid constructs may be provided in which the coding sequences for the proteins described herein are linked to IgE signal peptide. In some embodiments, proteins described herein are linked to IgE signal peptide.

In some embodiments for which protein is used, for example, one having ordinary skill in the art can, using well known techniques, produce and isolate proteins of the invention using well known techniques. In some embodiments for which protein is used, for example, one having ordinary skill in the art can, using well known techniques, inserts DNA molecules that encode a protein of the invention into a commercially available expression vector for use in well known expression systems. For example, the commercially available plasmid pSE420 (Invitrogen, San Diego, Calif.) may be used for production of protein in *Escherichia coli* (*E. coli*). The commercially available plasmid pYES2 (Invitrogen, San Diego, Calif.) may, for example, be used for production in *Saccharomyces cerevisiae* strains of yeast. The commercially available MAXBAC™ complete baculovirus expression system (Invitrogen, San Diego, Calif.) may, for example, be used for production in insect cells. The commercially available plasmid pcDNA or pcDNA3 (Invitrogen, San Diego, Calif.) may, for example, be used for production in mammalian cells such as Chinese hamster ovary (CHO) cells. One having ordinary skill in the art can use these commercial expression vectors and systems or others to produce protein by routine techniques and readily available starting materials. (See e.g., Sambrook et al., Molecular Cloning a Laboratory Manual, Second Ed. Cold Spring Harbor Press (1989)). Thus, the desired proteins can be prepared in both prokaryotic and eukaryotic systems, resulting in a spectrum of processed forms of the protein.

One having ordinary skill in the art may use other commercially available expression vectors and systems or produce vectors using well known methods and readily available starting materials. Expression systems containing the requisite control sequences, such as promoters and polyadenylation signals, and preferably enhancers are readily available and known in the art for a variety of hosts. See e.g., Sambrook et al., Molecular Cloning a Laboratory Manual, Second Ed. Cold Spring Harbor Press (1989). Genetic constructs include the protein coding sequence operably linked to a promoter that is functional in the cell line, or cells of targeted tissue, into which the constructs are transfected. Examples of constitutive promoters include promoters from cytomegalovirus (CMV) or SV40. Examples of inducible promoters include mouse mammary leukemia virus or metallothionein promoters. Those having ordinary skill in the art can readily produce genetic constructs useful for transfecting cells with DNA that encodes protein of the invention from readily available starting materials. The expression vector including the DNA that encodes the protein is used to transform the compatible host which is then cultured and maintained under conditions wherein expression of the foreign DNA takes place.

The protein produced is recovered from the culture, either by lysing the cells or from the culture medium as appropriate and known to those in the art. One having ordinary skill in the art can, using well known techniques, isolate protein that is produced using such expression systems. The methods of purifying protein from natural sources using antibodies which specifically bind to a specific protein as described above may be equally applied to purifying protein produced by recombinant DNA methodology.

In addition to producing proteins by recombinant techniques, automated peptide synthesizers may also be employed to produce isolated, essentially pure protein. Such techniques are well known to those having ordinary skill in the art and are useful if derivatives which have substitutions not provided for in DNA-encoded protein production.

The nucleic acid molecules may be delivered using any of several well known technologies including DNA injection (also referred to as DNA vaccination) with and without in vivo electroporation, liposome mediated, nanoparticle facilitated, recombinant vectors such as recombinant adenovirus, recombinant adenovirus associated virus and recombinant vaccinia. Preferably, the nucleic acid molecules such as the DNA plasmids described herein are delivered via DNA injection and along with in vivo electroporation.

Routes of administration include, but are not limited to, intramuscular, intranasally, intraperitoneal, intradermal, subcutaneous, intravenous, intraarterially, intraoccularly and oral as well as topically, transdermally, by inhalation or suppository or to mucosal tissue such as by lavage to vaginal, rectal, urethral, buccal and sublingual tissue. Preferred routes of administration include intramuscular, intraperitoneal, intradermal and subcutaneous injection. Genetic constructs may be administered by means including, but not limited to, traditional syringes, needleless injection devices, "microprojectile bombardment gone guns", or other physical methods such as electroporation ("EP"), "hydrodynamic method", or ultrasound.

Examples of electroporation devices and electroporation methods preferred for facilitating delivery of the DNA vaccines of the present invention, include those described in U.S. Pat. No. 7,245,963 by Draghia-Akli, et al., U.S. Patent Pub. 2005/0052630 submitted by Smith, et al., the contents of which are hereby incorporated by reference in their entirety. Also preferred, are electroporation devices and electroporation methods for facilitating delivery of the DNA vaccines provided in co-pending and co-owned U.S. patent application Ser. No. 11/874,072, filed Oct. 17, 2007, which claims the benefit under 35 USC 119(e) to U.S. Provisional Applications Ser. Nos. 60/852,149, filed Oct. 17, 2006, and 60/978,982, filed Oct. 10, 2007, all of which are hereby incorporated in their entirety.

U.S. Pat. No. 7,245,963 by Draghia-Akli, et al. describes modular electrode systems and their use for facilitating the introduction of a biomolecule into cells of a selected tissue in a body or plant. The modular electrode systems comprise a plurality of needle electrodes; a hypodermic needle; an electrical connector that provides a conductive link from a programmable constant-current pulse controller to the plurality of needle electrodes; and a power source. An operator can grasp the plurality of needle electrodes that are mounted on a support structure and firmly insert them into the selected tissue in a body or plant. The biomolecules are then delivered via the hypodermic needle into the selected tissue. The programmable constant-current pulse controller is activated and constant-current electrical pulse is applied to the plurality of needle electrodes. The applied constant-current electrical pulse facilitates the introduction of the biomolecule into the cell between the plurality of electrodes. The entire content of U.S. Pat. No. 7,245,963 is hereby incorporated by reference.

U.S. Patent Pub. 2005/0052630 submitted by Smith, et al. describes an electroporation device which may be used to effectively facilitate the introduction of a biomolecule into cells of a selected tissue in a body or plant. The electroporation device comprises an electro-kinetic device ("EKD device") whose operation is specified by software or firmware. The EKD device produces a series of programmable constant-current pulse patterns between electrodes in an array based on user control and input of the pulse parameters, and allows the storage and acquisition of current waveform data. The electroporation device also comprises a replaceable electrode disk having an array of needle electrodes, a central injection channel for an injection needle, and a removable guide disk. The entire content of U.S. Patent Pub. 2005/0052630 is hereby incorporated by reference.

The electrode arrays and methods described in U.S. Pat. No. 7,245,963 and U.S. Patent Pub. 2005/0052630 are adapted for deep penetration into not only tissues such as muscle, but also other tissues or organs. Because of the configuration of the electrode array, the injection needle (to deliver the biomolecule of choice) is also inserted completely into the target organ, and the injection is administered perpendicular to the target issue, in the area that is pre-delineated by the electrodes The electrodes described in U.S. Pat. No. 7,245,963 and U.S. Patent Pub. 2005/005263 are preferably 20 mm long and 21 gauge.

The following is an example of methods of the present invention, and is discussed in more detail in the patent references discussed above: electroporation devices can be configured to deliver to a desired tissue of a mammal a pulse of energy producing a constant current similar to a preset current input by a user. The electroporation device comprises an electroporation component and an electrode assembly or handle assembly. The electroporation component can include and incorporate one or more of the various elements of the electroporation devices, including: controller, current waveform generator, impedance tester, waveform logger, input element, status reporting element, communication port, memory component, power source, and power switch. The electroporation component can function as one element of the electroporation devices, and the other elements are separate elements (or components) in communication with the electroporation component. In some embodiments, the electroporation component can function as more than one element of the electroporation devices, which can be in communication with still other elements of the electroporation devices separate from the electroporation component. The present invention is not limited by the elements of the electroporation devices existing as parts of one electromechanical or mechanical device, as the elements can function as one device or as separate elements in communication with one another. The electroporation component is capable of delivering the pulse of energy that produces the constant current in the desired tissue, and includes a feedback mechanism. The electrode assembly includes an electrode array having a plurality of electrodes in a spatial arrangement, wherein the electrode assembly receives the pulse of energy from the electroporation component and delivers same to the desired tissue through the electrodes. At least one of the plurality of electrodes is neutral during delivery of the pulse of energy and measures impedance in the desired tissue and communicates the impedance to the electroporation component. The feedback mechanism can receive the measured impedance and can adjust the pulse of energy delivered by the electroporation component to maintain the constant current.

In some embodiments, the plurality of electrodes can deliver the pulse of energy in a decentralized pattern. In some embodiments, the plurality of electrodes can deliver the pulse of energy in the decentralized pattern through the control of the electrodes under a programmed sequence, and the programmed sequence is input by a user to the electroporation component. In some embodiments, the programmed sequence comprises a plurality of pulses delivered in sequence, wherein each pulse of the plurality of pulses is delivered by at least two active electrodes with one neutral electrode that measures impedance, and wherein a subsequent pulse of the plurality of pulses is delivered by a different one of at least two active electrodes with one neutral electrode that measures impedance.

In some embodiments, the feedback mechanism is performed by either hardware or software. Preferably, the feedback mechanism is performed by an analog closed-loop circuit. Preferably, this feedback occurs every 50 μs, 20 μs, 10 μs or 1 μs, but is preferably a real-time feedback or instantaneous (i.e., substantially instantaneous as determined by available techniques for determining response time). In some embodiments, the neutral electrode measures the impedance in the desired tissue and communicates the impedance to the feedback mechanism, and the feedback mechanism responds to the impedance and adjusts the pulse of energy to maintain the constant current at a value similar to the preset current. In some embodiments, the feedback mechanism maintains the constant current continuously and instantaneously during the delivery of the pulse of energy.

A pharmaceutically acceptable excipient can include such functional molecules as vehicles, adjuvants, carriers or diluents, which are known and readily available to the public. Preferably, the pharmaceutically acceptable excipient is an adjuvant or transfection facilitating agent. In some embodiments, the nucleic acid molecule, or DNA plasmid, is delivered to the cells in conjunction with administration of a polynucleotide function enhancer or a genetic vaccine facilitator agent (or transfection facilitating agent). Polynucleotide function enhancers are described in U.S. Pat. Nos. 5,593,972, 5,962,428 and International Application Serial Number PCT/US94/00899 filed Jan. 26, 1994, which are each incorporated herein by reference. Genetic vaccine facilitator agents are described in U.S. Ser. No. 021,579 filed Apr. 1, 1994, which is incorporated herein by reference. The transfection facilitating agent can be administered in conjunction with nucleic acid molecules as a mixture with the nucleic acid molecule or administered separately simultaneously, before or after administration of nucleic acid molecules. Examples of transfection facilitating agents includes surface active agents such as immune-stimulating complexes (ISCOMS), Freunds incomplete adjuvant, LPS analog including monophosphoryl lipid A, muramyl peptides, quinone analogs and vesicles such as squalene and squalene, and hyaluronic acid may also be used administered in conjunction with the genetic construct. In some embodiments, the DNA plasmid vaccines may also include a transfection facilitating agent such as lipids, liposomes, including lecithin liposomes or other liposomes known in the art, as a DNA-liposome mixture (see for example W09324640), calcium ions, viral proteins, polyanions, polycations, or nanoparticles, or other known transfection facilitating agents. Preferably, the transfection facilitating agent is a polyanion, polycation, including poly-L-glutamate (LGS), or lipid.

In some preferred embodiments, the DNA plasmids are delivered with an adjuvant that are genes for proteins which further enhance the immune response against such target proteins. Examples of such genes are those which encode other cytokines and lymphokines such as alpha-interferon, gamma-interferon, platelet derived growth factor (PDGF), TNFα, TNFβ, GM-CSF, epidermal growth factor (EGF), IL-1, IL-2, IL-4, IL-5, IL-6, IL-10, IL-12, IL-18, MHC, CD80, CD86 and IL-15 including IL-15 having the signal sequence deleted and optionally including the signal peptide from IgE. Other genes which may be useful include those encoding: MCP-1, MIP-1□, MIP-1p, IL-8, RANTES, L-selectin, P-selectin, E-selectin, CD34, GlyCAM-1, MadCAM-1, LFA-1, VLA-1, Mac-1, pl50.95, PECAM, ICAM-1, ICAM-2, ICAM-3, CD2, LFA-3, M-CSF, G-CSF, IL-4, mutant forms of IL-18, CD40, CD40L, vascular growth factor, fibroblast growth factor, IL-7, nerve growth factor, vascular endothelial growth factor, Fas, TNF receptor, Flt, Apo-1, p55, WSL-1, DR3, TRAMP, Apo-3, AIR, LARD, NGRF, DR4, DR5, KILLER, TRAIL-R2, TRICK2, DR6, Caspase ICE, Fos, c-jun, Sp-1, Ap-1, Ap-2, p38, p65Rel, MyD88, IRAK, TRAF6, IkB, Inactive NIK, SAP K, SAP-1, JNK, interferon response genes, NFkB, Bax, TRAIL, TRAILrec, TRAILrecDRC5, TRAIL-R3, TRAIL-R4, RANK, RANK LIGAND, Ox40, Ox40 LIGAND, NKG2D, MICA, MICB, NKG2A, NKG2B, NKG2C, NKG2E, NKG2F, TAP1, TAP2 and functional fragments thereof.

The DNA plasmid vaccines according to the present invention comprise DNA quantities of from about 1 nanogram to 10 milligrams; about 1 microgram to about 10 milligrams; or preferably about 0.1 microgram to about 10 milligrams; or more preferably about 100 microgram to about 1 milligram. In some preferred embodiments, DNA plasmid vaccines according to the present invention comprise about 5 nanogram to about 1000 micrograms of DNA. In some preferred embodiments, the DNA plasmid vaccines contain about 10 nanograms to about 800 micrograms of DNA. In some preferred embodiments, the DNA plasmid vaccines contain about 0.1 to about 500 micrograms of DNA. In some preferred embodiments, the DNA plasmid vaccines contain about 1 to about 350 micrograms of DNA. In some preferred embodiments, the DNA plasmid vaccines contain about 25 to about 250 micrograms of DNA. In some preferred embodiments, the DNA plasmid vaccines contain about 100 microgram to about 1 milligram DNA.

The DNA plasmid vaccines according to the present invention are formulated according to the mode of administration to be used. In cases where DNA plasmid vaccines are injectable compositions, they are sterile, and/or pyrogen free and/or particulate free. An isotonic formulation is preferably used. Generally, additives for isotonicity can include sodium chloride, dextrose, mannitol, sorbitol and lactose. In some cases, isotonic solutions such as phosphate buffered saline are preferred. Stabilizers include gelatin and albumin. In some embodiments, a vasoconstriction agent is added to the formulation. In some embodiments, a stabilizing agent that allows the formulation to be stable at room or ambient temperature for extended periods of time, such as LGS or other polycations or polyanions is added to the formulation.

In some embodiments, methods of eliciting an immune response in mammals against a consensus dengue antigen include methods of inducing mucosal immune responses. Such methods include administering to the mammal one or more of CTACK protein, TECK protein, MEC protein and functional fragments thereof or expressible coding sequences thereof in combination with an DNA plasmid including a consensus dengue antigen, described above. The one or more of CTACK protein, TECK protein, MEC protein and functional fragments thereof may be administered prior to, simultaneously with or after administration of the DNA plasmid dengue vaccines provided herein. In some embodiments, an isolated nucleic acid molecule that encodes one or more proteins of selected from the group consisting of: CTACK, TECK, MEC and functional fragments thereof is administered to the mammal.

EXAMPLES

The present invention is further illustrated in the following Examples. It should be understood that these Examples, while indicating preferred embodiments of the invention, are given by way of illustration only. From the above discussion and these Examples, one skilled in the art can ascertain the essential characteristics of this invention, and without departing from the spirit and scope thereof, can make various changes and modifications of the invention to adapt it to various usages and conditions. Thus, various modifications of the invention in addition to those shown and described herein will be apparent to those skilled in the art from the foregoing description. Such modifications are also intended to fall within the scope of the appended claims.

Preferably the DNA formulations for use with a muscle or skin EP device described herein have high DNA concentrations, preferably concentrations that include microgram to tens of milligram quantities, and preferably milligram quantities, of DNA in small volumes that are optimal for delivery to the skin, preferably small injection volume, ideally 25-200 microliters (μL). In some embodiments, the DNA formulations have high DNA concentrations, such as 1 mg/mL or greater (mg DNA/volume of formulation). More preferably, the DNA formulation has a DNA concentration that provides for gram quantities of DNA in 200 μL of formula, and more preferably gram quantities of DNA in 100 μL of formula.

The DNA plasmids for use with the EP devices of the present invention can be formulated or manufactured using a combination of known devices and techniques, but preferably they are manufactured using an optimized plasmid manufacturing technique that is described in U.S. application Ser. No. 12/126,611 which published as US Publication No. 20090004716, which published Jan. 1, 2009. In some examples, the DNA plasmids used in these studies can be formulated at concentrations greater than or equal to 10 mg/mL. The manufacturing techniques also include or incorporate various devices and protocols that are commonly known to those of ordinary skill in the art, in addition to those described in US Publication No. 20090004716 and those described in U.S. Pat. No. 7,238,522, which issued on Jul. 3, 2007. The high concentrations of plasmids used with the skin EP devices and delivery techniques described herein allow for administration of plasmids into the ID/SC space in a reasonably low volume and aids in enhancing expression and immunization effects. The publications, US Publication No. 20090004716 and U.S. Pat. No. 7,238,522, are hereby incorporated in their entirety.

Example 1

Dengue DIII Expression Constructs

Approximately 15 subtype sequences were collected from different geographical populations from GeneBank to avoid sampling bias. All sequences used were non-recombinant. Multiple alignment of Dengue envelope (Dengue E) DIII sequences was carried out using the application Clustal X (version 1.81), in which pair-wise alignment parameters were set to the dynamic slow-accurate programming, using 10 as the gap opening penalty and 0.1 as the gap extension penalty. Multiple alignment parameters included a gap extension penalty equal to 0.2. The Dengue E consensus nucleotide sequence was obtained after performing multiple alignment and a few minor manual adjustments. Deduced amino acid sequences were used to guide the introduction of alignment gaps so that they were inserted between codons. Codon optimization and RNA optimization was performed by using GeneOptimizer (GENEART, Germany). The codon optimized synthetic sequence was further cloned into KpnI/PstI sites of pVAX mammalian expression plasmid.

Figure 4A:
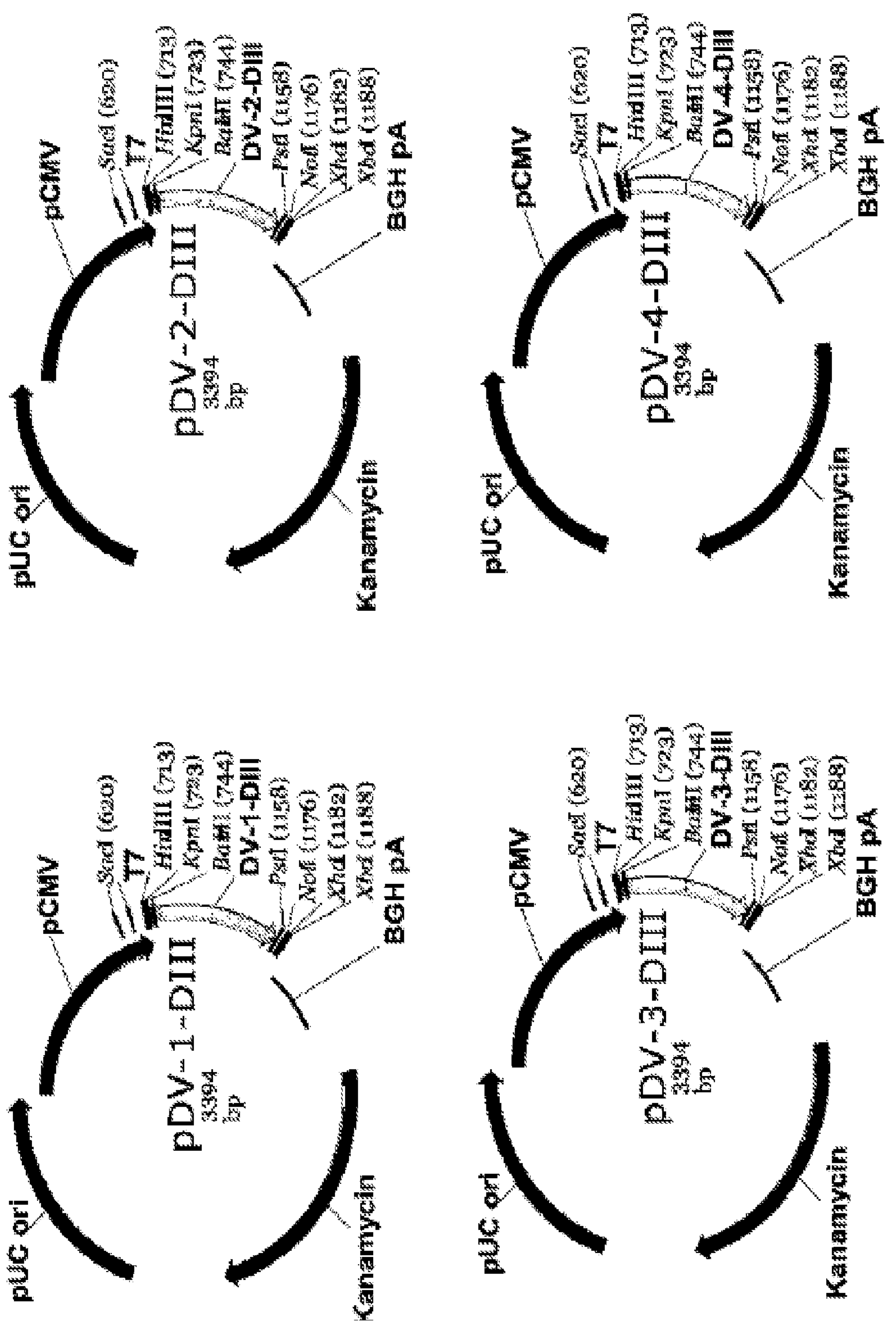
FIG. 4*a* displays plasmid maps for the four plasmids that each has one subtype DIII domain.

FIG. 1 illustrates the organization of Dengue polypeptide and the conformational features of Dengue E. Dengue E consists of three distinct domains: I, II and III. Amino acid sequences of Dengue E DIII domain were chosen from the NCBI database and aligned to generate consensus sequence: DV-1 DIII (SEQ ID NO: 1), DV-2 DIII (SEQ ID NO: 2), DV-3 DIII (SEQ ID NO: 3), and DV-4 DIII (SEQ ID NO: 4). The amino acid sequences from different strains were assembled for alignment using Lasergene 7 (DNA Star Inc, Madison, Wis.). An Ig-E leader sequence, preceded by a Kozak sequence, was fused to the N-terminus of the coding sequence. Based on the amino acid sequence, human optimized synthetic gene sequence was created using software tools by Geneart Inc and cloned into pVAX vector. The expression vectors encoding Dengue Envelope DIII domains of subtypes-1, -2, -3 and -4 are referred as pDV-1 DIII, pDV-2 DIII, pDV-3 DIII and pDV-4 DIII respectively. The plasmid maps are provided in FIG. 4*a*.

Figure 4B:
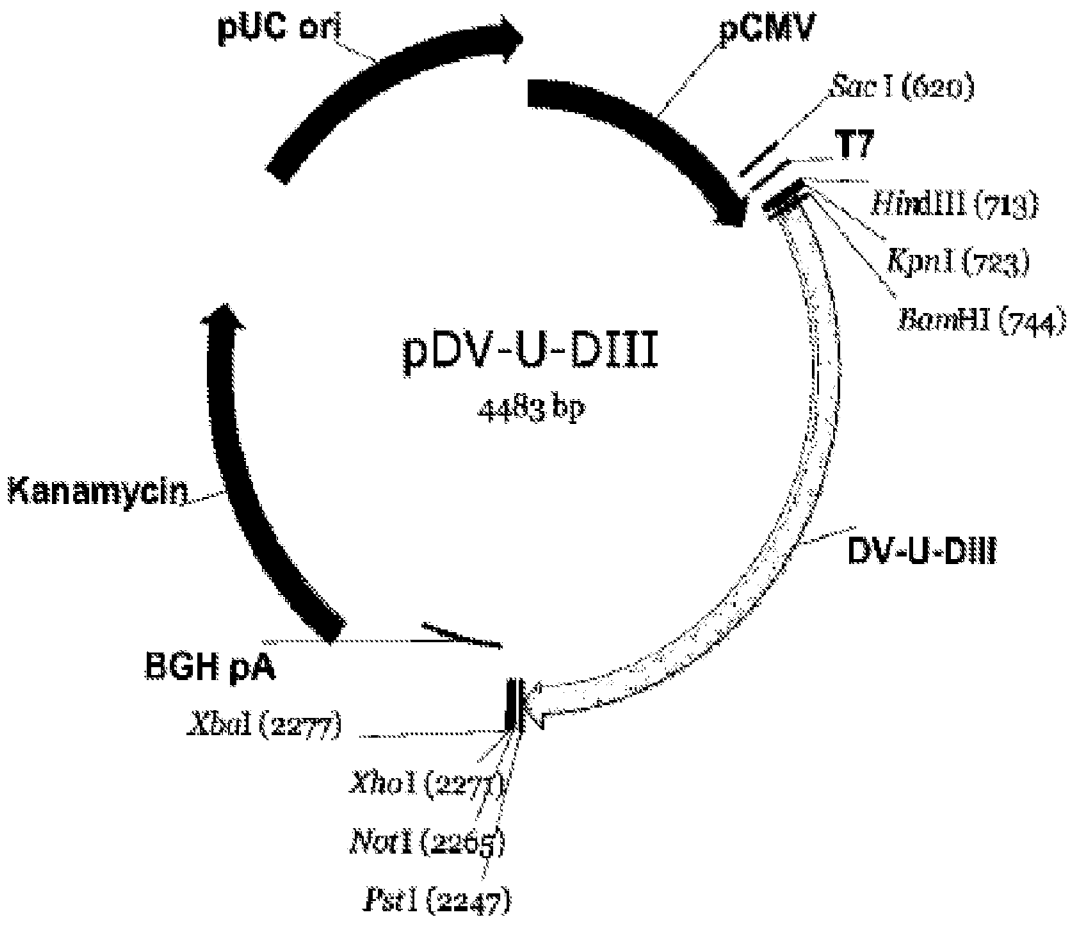
FIG. 4*b* displays plasmid maps for the plasmid that contains DV-U-DIII.

A construct combining all four DIII domains (universal or universal DIII) separated by proteolytic cleavage sequences was constructed and referred to as DV-U-DIII (SEQ ID NO: 5). FIG. 3 shows the schematic plans for the organization of the open reading frame, as well as the amino acid sequence based on which human optimized gene was synthesized. DV-U-DIII was cloned into pVAX vector to create a universal expression construct: pDV-U-DIII, which plasmid map can be seen in FIG. 4*b*.

Example 2

Expression of Dengue DIII Domain in the Mammalian System

*Aedes albopictus* C6/36 cells, Vero, HEK293, HeLa, RD and BHK cells were obtained from the American Type Culture Collection (Manassas, Va.). C6/36 cells were maintained in Eagle's minimum essential medium (EMEM; Gibco BRL) supplemented with 10% heat-inactivated fetal bovine serum (FBS), penicillin G (100 U/ml), streptomycine (100 ug/ml), L-glutamine and nonessential amino acids at 28 C in 5% CO2. Vero cells were maintained in Dulbecco's modified Eagle medium (DMEM)-F12 (Gibco BRL) containing 115 mM HEPES buffer supplemented with 10% heat inactivated fetal bovine serum, penicillin G (100 U/ml), streptomycin (100 ug/ml), L-glutamine and nonessential amino acids at 37° C. in 5 CO2. HEK293, HeLa and RD cells were maintained in DMEM medium supplemented with 10% heat inactivated fetal bovine serum, penicillin G (100 U/ml), streptomycin (100 ug/ml) at 37° C. in 5 CO2.

The viruses utilized included DENV 1 virus, DENV 2, prototype DENV 3(H 87 strain) and prototype DENV 4 (H241). All experiments with the Dengue virus used clinical virus isolates and stocks that had been passaged in cell culture fewer than four times. Viral stocks were obtained by inoculating a monolayer of C6/36 cells in a 75-$cm^2$ tissue culture flask with 200 ul of virus diluted in 1 ml of EMEM-2% FBS. After one hour, 14 ml of EMEM supplemented with 2% FBS was added and the cells were cultures for 10 days at 28 C at 5% CO2. The supernatant was removed from the cells and centrifuged for 5 min at 2000×g to pellet cellular debris. The supernatant was aliquoted and stored at 80° C. DENV 1 was grown and passaged in Vero cells, whereas DENV 4 (H241) was grown in C6/36 cells as described above and passaged one time in Vero cells.

Figure 5:
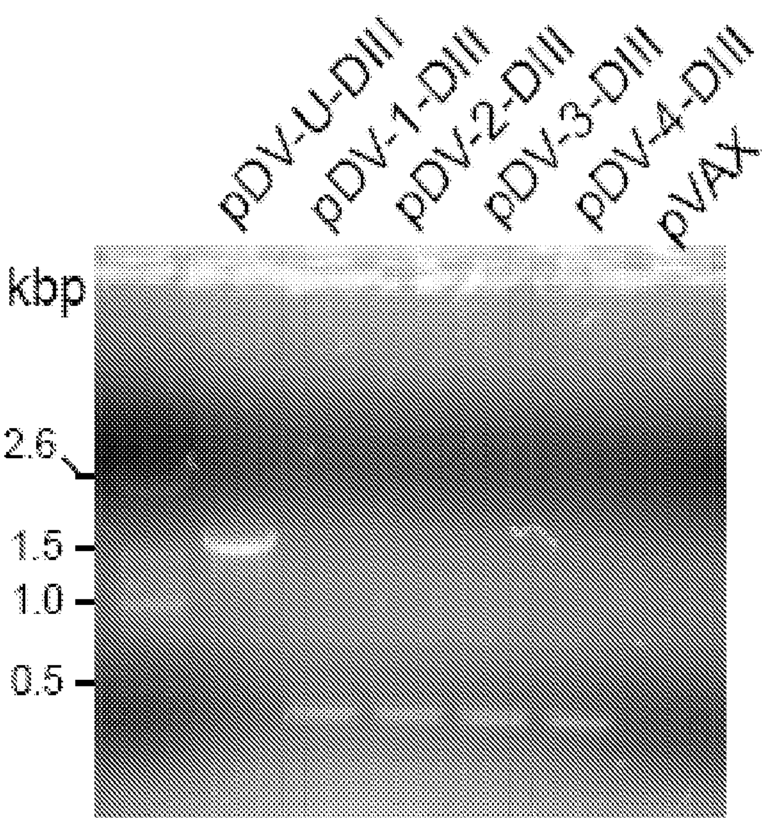
FIG. 5 displays gel photograph showing DIII mRNA transcripts in cells expressing DIII from all four subtypes and DV-U fragments cloned into pVAX.

RT-PCR method was utilized to detect the presence of mRNA transcripts coding for DIII domains, since pVAX-based Dengue DIII vaccine constructs do not include additional synthetic epitopes. A human rhabdomyosarcoma cell line, RD cells, were transfected with the DIII-expression constructs (independently, each one of four serotypes and the universal) and two days after transfection, total RNA was prepared from the transfected cells. Using specific primers for each of Dengue virus serotypes, RT-PCR was carried out to amplify respective DIII domains. FIG. 5 is a photo of a gel that shows the amplified DIII fragments from the transfected cells, represented by the bands that represent fragments of 360 bp in length. Mock-transfected cells (transfected with empty pVAX vector) did not show such amplified products. This study confirms the presence of mRNA transcripts for DIII expression from transfected cells. Thus these DNA constructs suggest expression of protein products.

In addition to these pVAX-based DNA constructs, an additional set of DNA constructs were constructed to express similar protein products. These constructs included a fusion of Dengue virus DIII domain and a synthetic FLAG (Sigma Co.) epitope for immunodetection purposes (referred to as FLAGGED-Constructs). RD cells were transfected with FLAGGED-constructs and thirty six hours after transfection, the cells were analyzed with an immunofluorescent assay using an anti-FLAG monoclonal antibody (Sigma Co.).

Figure 6:
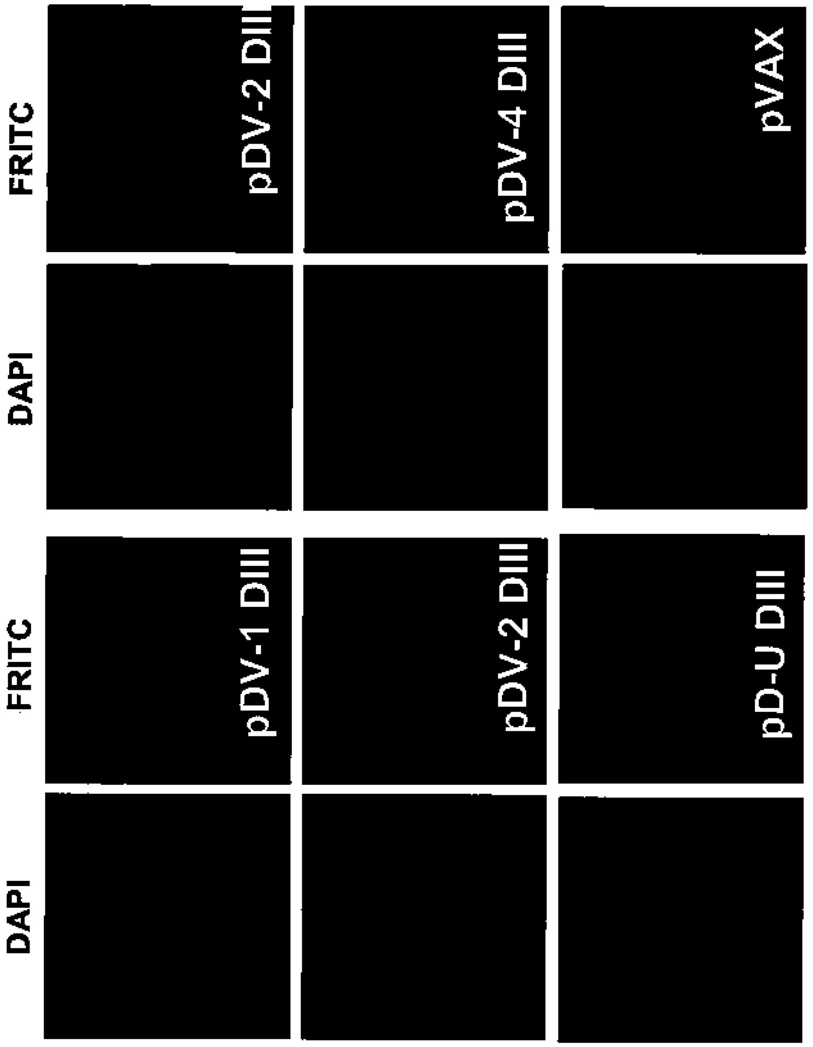
FIG. 6 displays photographs of indirect immunofluorescent analysis (IFA) of expression of DV DIII vaccine constructs, which have FLAGGED-epitope, in RD cells.
Figure 7:
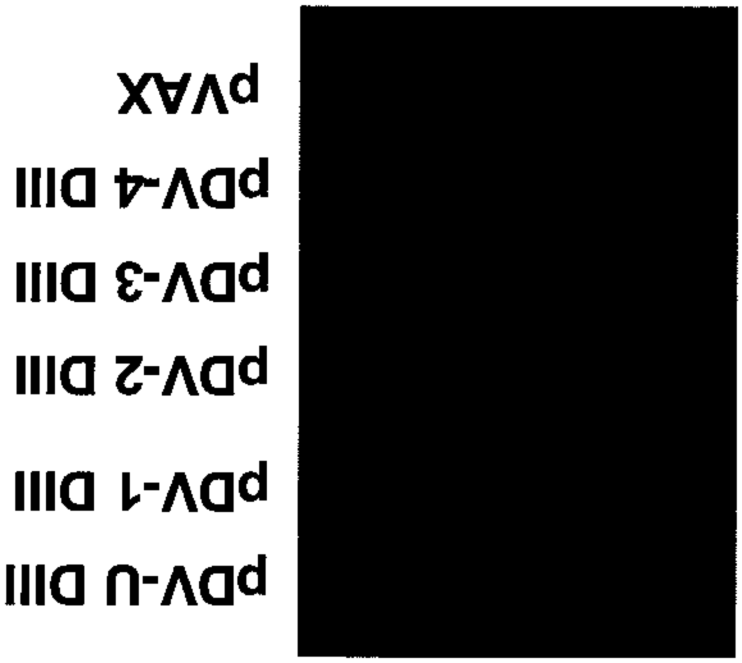
FIG. 7 displays a gel photograph showing the in vitro translation of DIII products.

The expression pattern for all of the four DIII domains, individually, and the combined DIII domain, or universal DIII (or universal dengue antigen), from pDV-U-DIII was identical, as evidenced from the cytoplasmic localization pattern of the protein (See FIG. 6). It has been well documented by several reports that the expression of full length Dengue E yields a typical cytoplasmic pattern. Thus, the expression pattern of DIII, alone, agrees with that of full length Dengue E. Radiolabeled Dengue E DIII-proteins were generated from these FLAGGED-Constructs and resolved in a SDS-PAGE gel. The mobility of these proteins corresponds to a protein with a mass around 16 kDa, as shown in the gel photo of FIG. 7. The molecular mass of the combined DIII domains appeared to be approximately 50 kDa in mass.

Example 3

Figure 8:
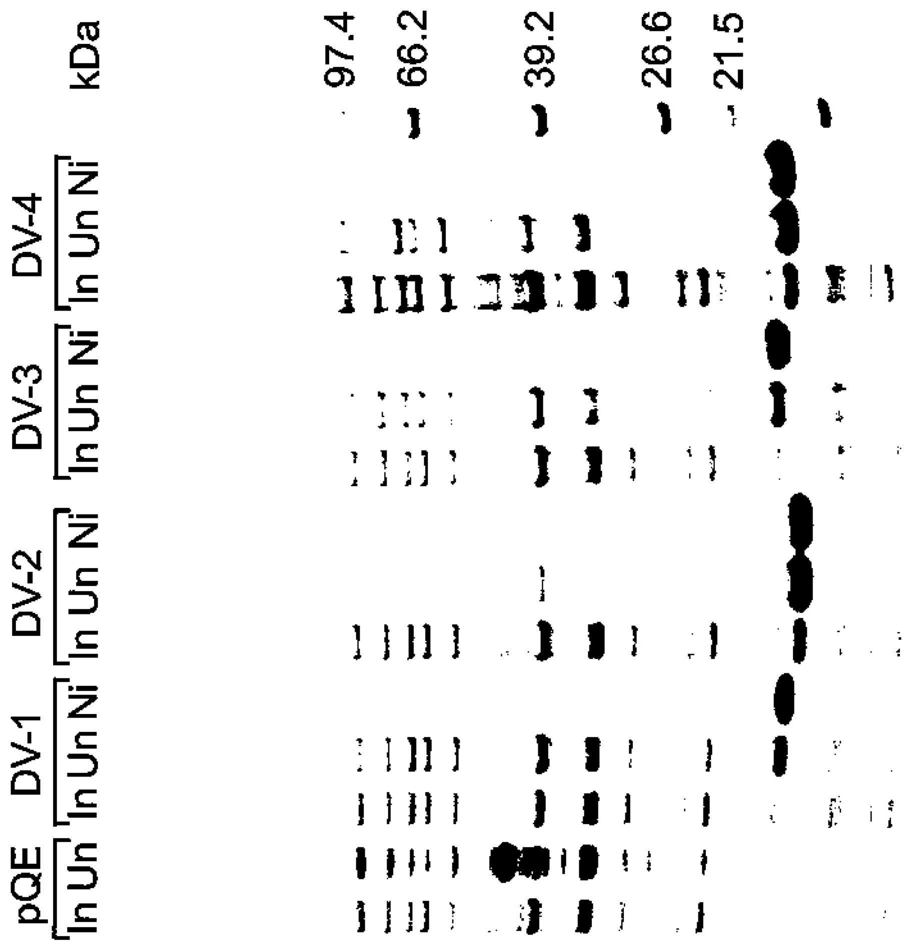
FIG. 8 displays a SDS-PAGE gel of *E. coli* lysates and Ni-column purified samples detecting DIII production.

Synthesis and Production of DENV E DIII Protein from all of Four Subtypes Using Bacterial Expression and Purification System The envelope region (295-415) that represents the DIII domain of all four Dengue serotypes was expressed in *E. coli* by transformation with pQE vector including an encoding DIII domain. The predicted sizes of Dengue E-DIII are about 16 kDa. SDS-PAGE (SDS-poly acrylamide gel electrophoresis) of the bacterial lysates showed over-expressed proteins of expected size in (Isopropyl β-D-1-thiogalactopyranoside) IPTG-induced *E. coli* cultures. IPTG is commonly used as a molecular mimic of allolactose to induce the activity of beta-lactosidase. Further, the appearance of the protein band that appears in the Ni-column (Ni-chelated column with the ability to bind polyhistidine-tagged recombinant proteins) eluted fraction corresponds to the mobility of the prominent band that appears in the column with IPTG-treated lysates. The lysates from pQE-vector transformed samples of both untreated and IPTG-treated samples (FIG. 8, first two lanes) failed to show the protein band that corresponds to the DIII domains. This result confirms that the purified proteins are the Dengue DIII domains expressed from pQE vector-expressing constructs upon induction from IPTG (FIG. 8).

Example 4

Figure 9:
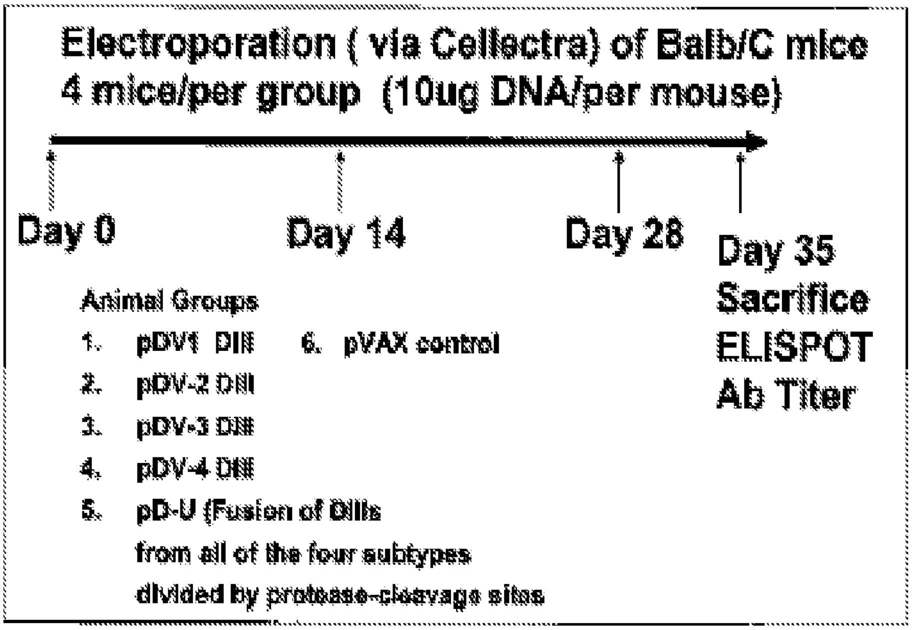
FIG. 9 displays a timeline of the vaccination scheme for DV.

Immunization of Mice Via EP (Using Cellectra) with pDV-U-DIII Vaccine Candidate and the Specificity of DV-U-DIII Sera against DIII Domains Mice were immunized with the plasmid DNA constructs (as described in Example 1, above) according to the schedule illustrated in FIG. 9.

Groups (n=4) of 4-week-old Balb/c mice were immunized intramuscularly with 15 ug pDV-U DIII and remaining individual DIII expressing vectors. pVAX was used as the control vector. Before immunization, pre-immunized blood samples were collected using standing protocols for bleeding through the veins in the eye. Square-wave pulses were used in all experiments (Draghia-Akli and Smith, 2003) and delivered with the constant-current CELLECTRA® electroporator (VGX Pharmaceuticals, Blue Bell, Pa.). A three electrode array (3-EA) was used in the mouse experiments. The 3-EA consists of three 26-gauge solid stainless steel electrodes in an isosceles triangle formation, with the two long sides 0.5 mm in length and short side 0.3 mm in length, held together with a nonconductive plastic. Specific EP conditions for the mouse experiments were using constant current, 0.1 Amps, three pulses, 52 msec/pulse, 4 sec between pulses. The lag time between plasmid injection and EP was about 20 sec.

The sequence of events for plasmid administration/EP were performed as follows: a disposable electrode assembly was placed in the receptacle of the handle, the initiation button on the handle was pressed, the animal experimental group number was entered, 50 ul of DNA construct (15 ug total DNA) plasmid using insulin syringe was injected, needles were immediately placed into the area surrounding the injection site, the initiation button on the handle was pressed, and after 4 second countdown, pulses were delivered. After 5 seconds following electroporation, the array was gently removed from muscle. All electrodes were completely inserted into the muscle during all treatments. All DNA were prepared using endotoxin-free Qiagen columns. The animals were housed in a temperature-controlled, light-cycled facility at the University of Pennsylvania, and their care was under the guidelines of the National Institutes of Health and the University of Pennsylvania.

Figure 10:
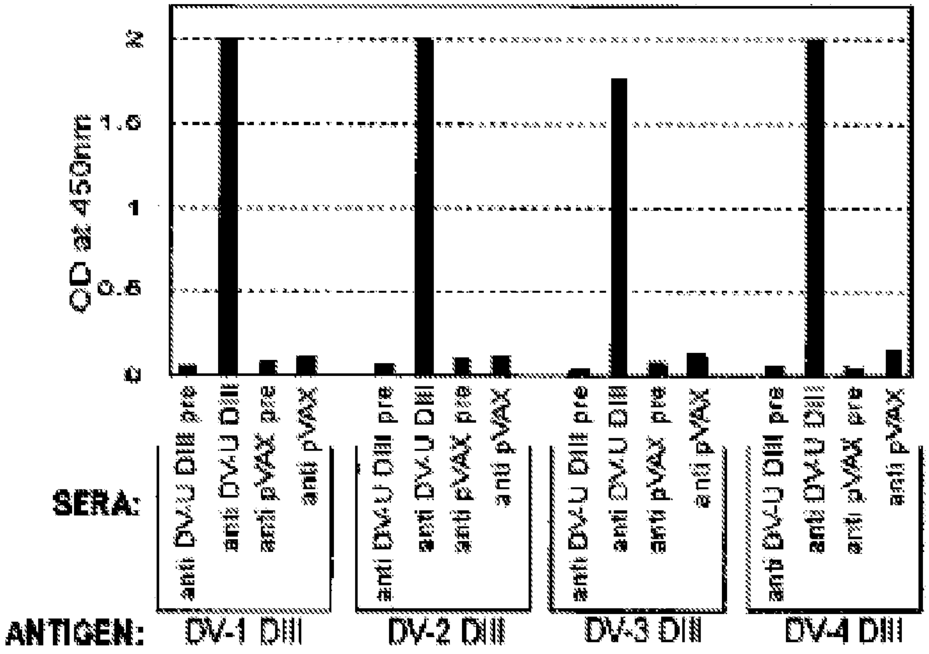
FIG. 10 displays a bar graph of spectroscopic readings that shows specific reaction between anti-DIII serum from pDV-U-DIII vaccinated mice and the DIII antigens from DV-1 through DV-4 captured onto Ni-coated ELISA plates.

Serum samples from individual mice obtained after the third booster were assayed for DENV antibody titers by ELISA. All mice made anti-DIII antibodies. The titers of anti-DENV E DIII antibodies generated by immunized mice were determined by ELISA assay using purified DIII fragments as capture antigens. The antigens were captured in Ni-coated ELISA plates and then tested against sera from pDV-U-DIII vaccinated mice. As shown in FIG. 10, sera from mice immunized with pDV-U-DIII displayed high levels of ELISA reactivity, whereas the reactivity of serum from pVAX-immunized mice was negligible (data not shown). Also there was a huge difference between pre- and post-pDV-U-DIII vaccinated mice, in terms of the generation of anti-DIII domain antibody. The level of the antibody titers generated by individual DIII-domain expression constructs was significantly lower than the antibody titer elicited by pDV-U-DIII vaccine candidate. Based on this ELISA data, we decided to proceed with the anti-DIII serum collected from the mice immunized with pDV-U-DIII vaccine candidate for all subsequent analysis.

Figure 11:
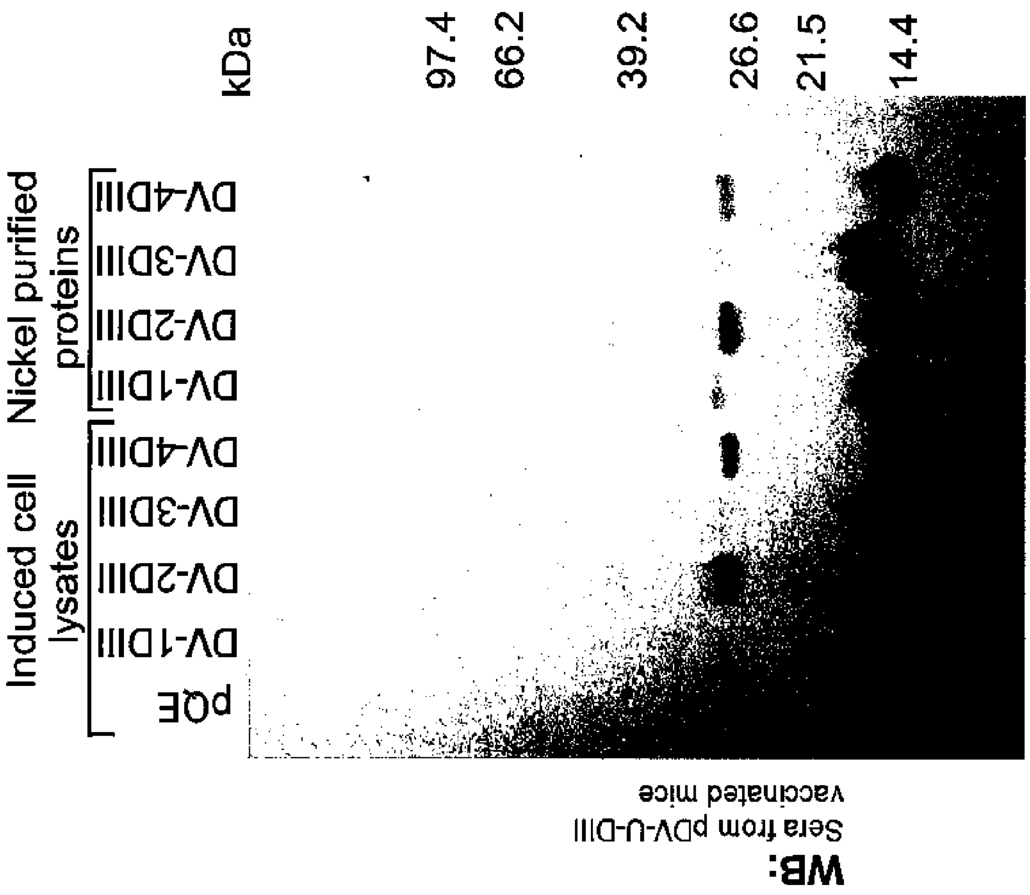
FIG. 11 displays a gel photograph showing immunodetection of DIII proteins by western blot analysis using anti-DIII serum from pDV-U-DIII vaccinated mice.

The ability of the sera collected from the mice immunized with pDV-U-DIII construct to react with DIII domains from all four serotypes was examined. The IPTG-induced bacterial lysates, as well as purified DIII domains of all four serotypes, were resolved in a SDS-PAGE gel and immunoprobed by western blotting analysis, using pDV-U-DIII serum as a potential anti-Dengue DIII sera. HRP-conjugated anti-mouse antibody was used to detect the antigen-antibody complex, and a chemiluminescent system was used to detect the immunoreaction. The D-U serum clearly recognized the DIII proteins from both IPTG-induced lysates as well as Ni-eluted samples for all four serotypes. Specific binding to the DIII antigen without binding to other protein samples from the crude lysate yields the direct evidence for the specific reaction between the serum and the DIII antigen (see resolved band, including multimer bands, in FIG. 11). The serum identified a molecule of about 16 kDa in mass which is equivalent to the mass exhibited by the purified DIII fragments.

DV-U-DIII serum was also examined to verify whether it can bind to the DIII antigens expressed in cells that were transfected with all four DIII domains individually. For this purpose, HeLa cells were transiently transfected with these DIII-encoding pVAX expression constructs and thirty six hours post transfection, the cells were fixed for immunofluorescence analysis.

First, the cells were transfected with Dengue vaccine constructs and pVAX (1 mg/well) using FuGENE 6 Transfection Reagent (Roche). After incubating transfected cells with anti-mouse Dengue antibody or the sera from the pDV-U DIII vaccinated mice for 90 min, the slides were incubated with tetramethyl rhodamine isothiocyanate-conjugated secondary antibody (Sigma-Aldrich) for 45 min. 40,6-Diamido-2-phenylindole hydrochloride (Sigma-Aldrich) was added to the solution of secondary antibody to counterstain nuclei to show the nuclei of the total number of cells available in the given field. The images were analyzed using the Phase 3 Pro program for fluorescent microscopy (Media Cybernetics, Silver Spring, Md.).

Figure 12:
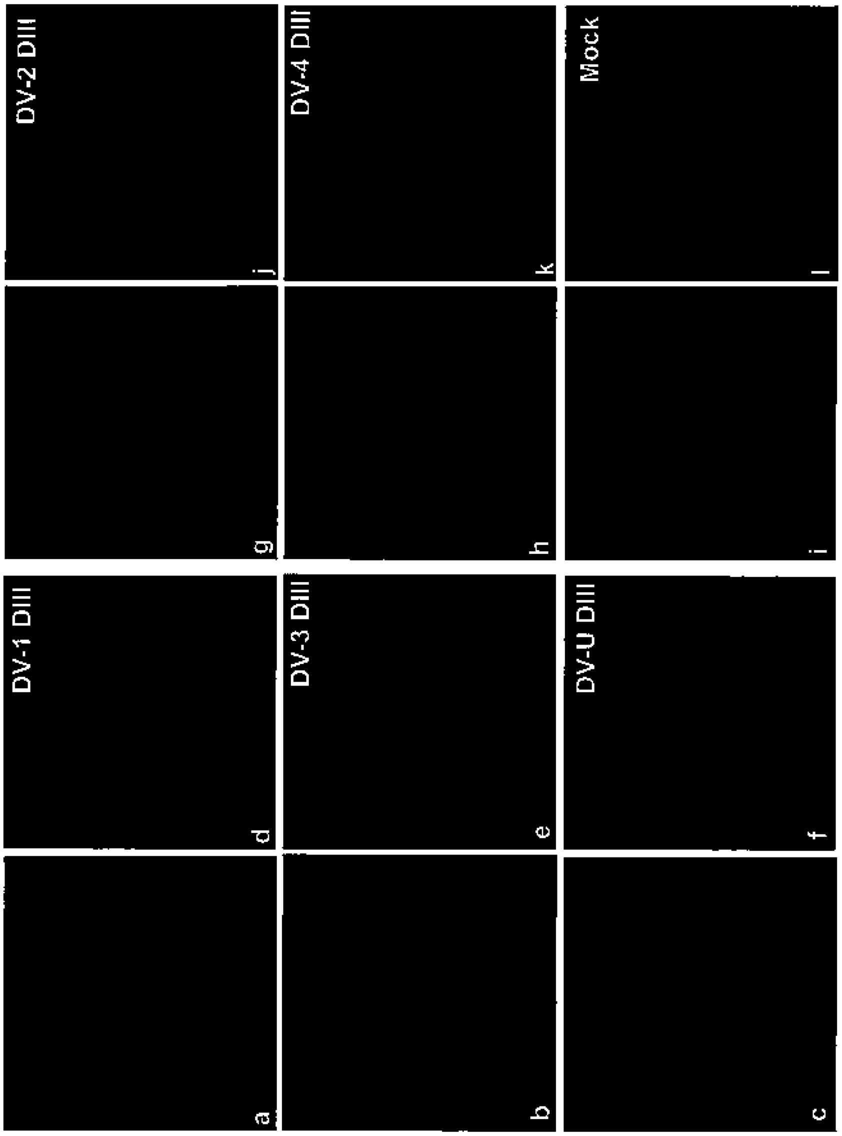
FIG. 12 displays photographs showing the specific staining of individual and combined DIII domains using anti-DIII serum from pDV-U-DIII vaccinated mice.

Anti-DV-U-DIII serum did not yield any significant staining with both untransfected and pVAX-transfected HeLa cells (received from ATCC, Va). However, DV-U-DIII-serum yielded highly specific staining with DIII-antigens alone (FIG. 12). Most importantly, the DIII-expressing cells revealed predominantly a cytoplasmic localization pattern. This observation is consistent with the immunofluorescent studies carried out with FLAG-epitope tagged DIII-expression vectors using anti-FLAG antibody that targeted DIII proteins fused with FLAG-epitope as shown in FIG. 6.

Example 5

The Binding of Anti-DIII Sera from pDV-U-DIII Vaccinated Mice to the Intact DIII Domain of E from Live Virions in Natural Conformation The DV-U DIII serum was tested against Dengue-2 infected cells to see whether the anti-DIII serum could react to Dengue-2 viruses. Naturally, DIII domains are believed to be situated in the peak region of Dengue E three-dimensional configuration on the outer surface of the viruses.

Figure 13:
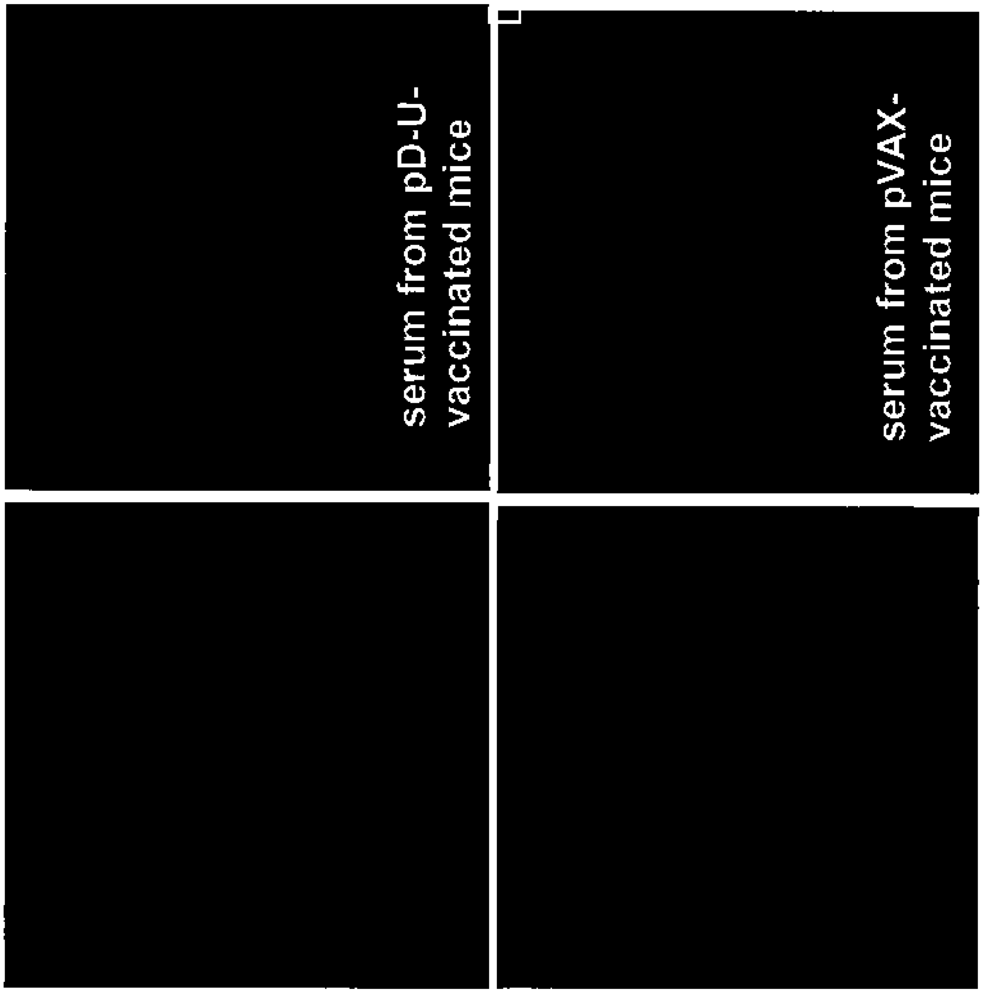
FIG. 13 displays photographs showing the staining of DV-2 infected Vero cells by sera from pDV-U-DIII vaccinated mice.

Dengue-2 virus was amplified in BHK-21 (baby hamster kidney cell line; ATCC, Manassas, Va.) cells to achieve high titers. Further, this high titer viral stock was used to infect Vero cells (ATTC, Manassas, Va.). After four days of infection, the Dengue-2 infected cells were stained with anti-DV-U DIII serum, followed by FITC-conjugated anti-mouse antibody, per the protocols outlined in above Example 4. Anti-DV-U DIII serum failed to yield any distinct staining pattern with uninfected cells. This serum reacted only to the cells infected by Dengue-2 subtype viruses. The serum collected from pVAX-vaccinated mice also did not react with both Dengue-2 infected and uninfected Vero cells. Thus, only DV-U-DIII vaccinated mice generated anti-DIII antibody that can recognize DIII domains of Dengue E (FIG. 13).

The DV-U DIII serum was tested against the cells infected with all four Dengue subtypes to see whether the anti-DIII serum could react to all of these four types of infected cells.

Figure 15:
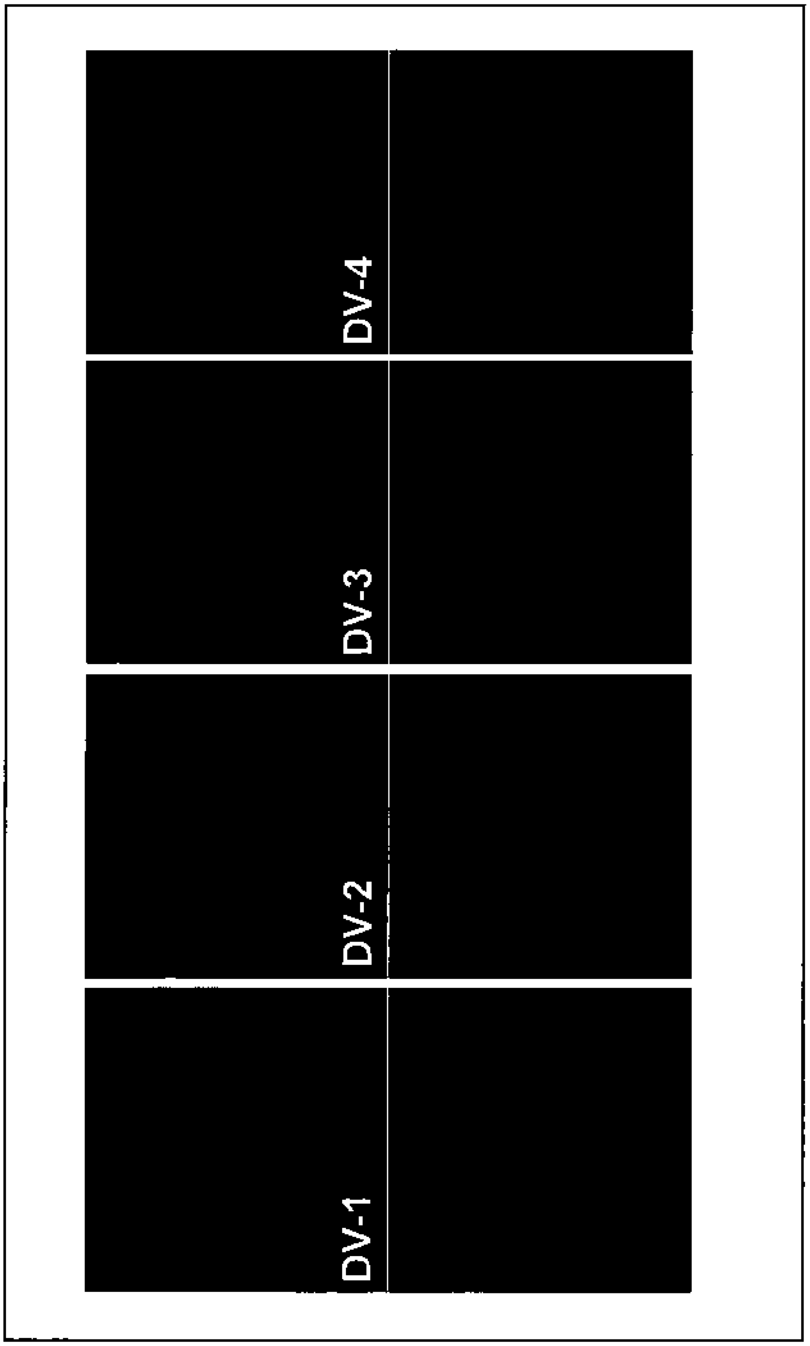
FIG. 15 displays photographs showing the staining of Dengue Virus infected cells with pDV-U DIII serum.

Vero cells grown overnight in chamber-slides were infected with high titer viral stocks of all four subtypes. After four days of infection, the Dengue infected cells were stained with anti-DV-U DIII serum, followed by FITC conjugated anti-mouse antibody as per the protocols outlined earlier. Anti-DV-U DIII serum failed to yield any distinct staining pattern with uninfected cells. This serum reacted only to the cells infected by Dengue subtypes. Interestingly the serum collected from pVAX-vaccinated mice also did not react with any of the Dengue-infected as well as uninfected Vero cells. Thus, only DV-U DIII vaccinated mice generated anti-DIII antibody that can recognize DIII domains of E from Dengue virions (FIG. 15). The upper panel indicates the infected cells and the bottom panel shows the same field with DAPI staining to indicate the nuclear contents of the cells available in the field. This observation not only indicates the specific interaction between anti-DIII antibody present in DV-U DIII vaccinated mice and the DIII antigen, but also indicates that this antibody can react to the intact DIII domain of E from Dengue virus itself in the natural conformation.

Example 6

Neutralizing Ability of Anti-DIII Serum Against Various Subtypes of Dengue Virus The neutralization ability of the sera generated against the pDV-U DIII or pre-immunized sera (control) on DENV1, -2, -3 and -4 infectivity was determined using plaque neutralization assay. The plaque reduction neutralization tests were performed using modified protocols from Russel et al (A Plaque Reduction Test for Dengue Virus Neutralizing Antibodies. 1967. p. 285-290), Kochel, T. J., et al. (Effect of dengue-1 antibodies on American dengue-2 viral infection and dengue haemorrhagic fever. The Lancet, 2002. 360(9329): p. 310-312) and Wu, S.-J. L., et al. (Detection of Dengue Viral RNA Using a Nucleic Acid Sequence-Based Amplification Assay. 2001. p. 2794-2798).

The viral stocks and different dilutions of anti-DIII serum from pDV-U-DIII vaccinated mice were mixed and the resulting mixture was made up to 200 micro liters of D10 medium (DMEM-medium supplemented with 10% Fetal bovine serum; Invitrogen) in Eppendorf tubes. These mixtures were kept in the incubator at 37° C. for one hour and then were added to the cells (cells were overnight-seeded on tissue culture chamber slides) to enable infection of Vero cells. After one hour of incubation with the viral mixtures, the cells were thoroughly washed with PBS and left in the incubation chamber for further incubation with cell media for four days. The controls for this assay included: (1) uninfected Vero cells, (2) cells infected with viral stock and not treated with any of the serum and (3) cells infected with viral stocks and treated with serum from pVAX-vaccinated mice.

Figure 14:
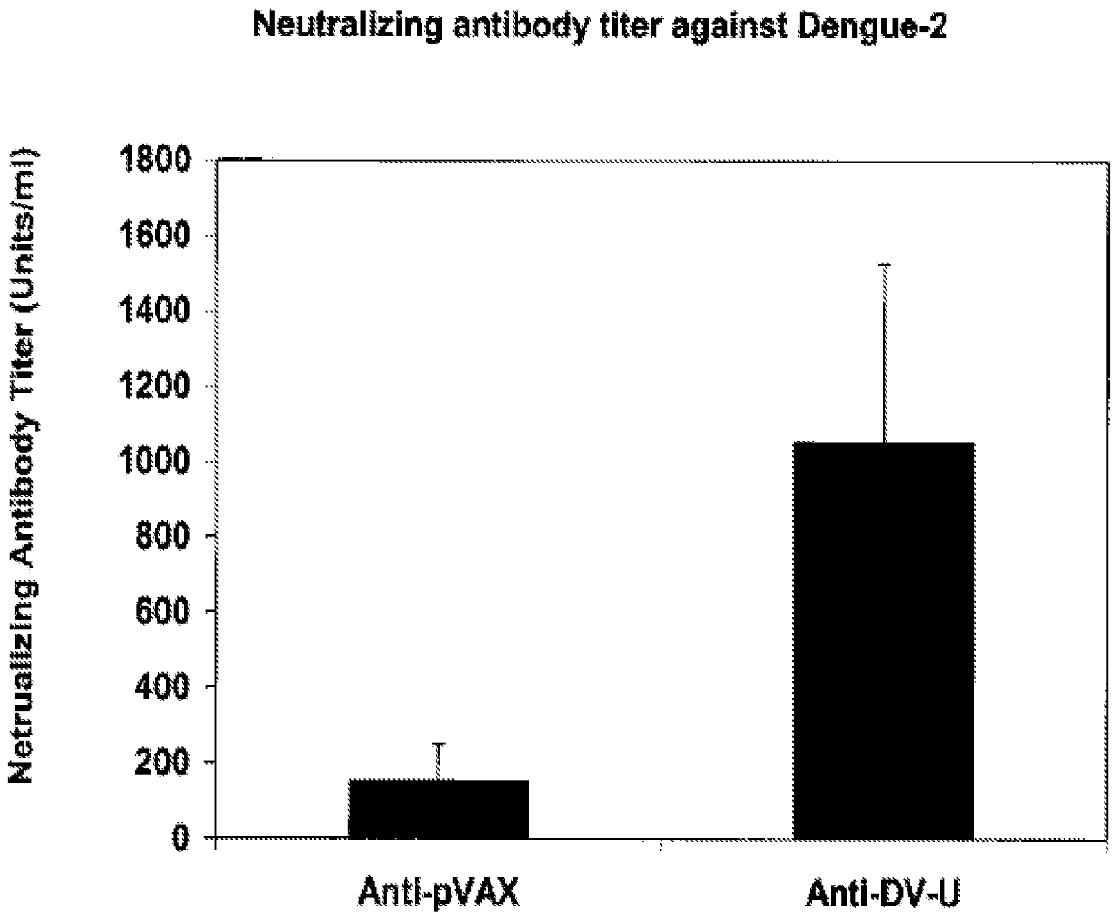
FIG. 14 displays a bar graph showing neutralizing antibody titer against DV-2.

The anti-DIII serum from pDV-U-DIII vaccinated mice stained Dengue-2 infected cells without any ambiguity (FIG. 13). In addition, the serum failed to yield any significant staining with uninfected cells. The highest number of infected cells by staining was observed with viral stocks that were not treated with any sera. The number of viral infected cells was found to be reduced in cells that were infected with anti-DIII sera-treated viral stocks than the cells that received untreated viral stocks. Thus, the treatment of viral stocks with the anti DIII sera reduced the titer of Dengue-2 virus, as seen in the bar graph shown in FIG. 14.

Similar neutralization results were achieved by using viral stock from Dengue-1, -3 and -4 subtypes instead of the Dengue-2 viral stock, used above. The anti-DIII serum from p-DV-U DIII vaccinated mice stained the cells infected with all four Dengue subtypes without any ambiguity. In addition, it was observed that the serum did not yield any significant staining with uninfected cells. The highest number of infected cells by staining was observed with viral stocks that were not treated with any sera. The number of viral infected cells was found to be significantly lower with the cells that were treated with anti-DIII sera-treated viral stocks than the cells that received untreated viral stocks. Thus, the treatment of viral stocks with the anti DIII sera reduced the titer of infectious Dengue virions. Therefore, the sera from pDV-U DIII vaccinated mice contained anti-DIII antibodies that showed neutralizing ability against all four dengue subtypes.

Figure 16:
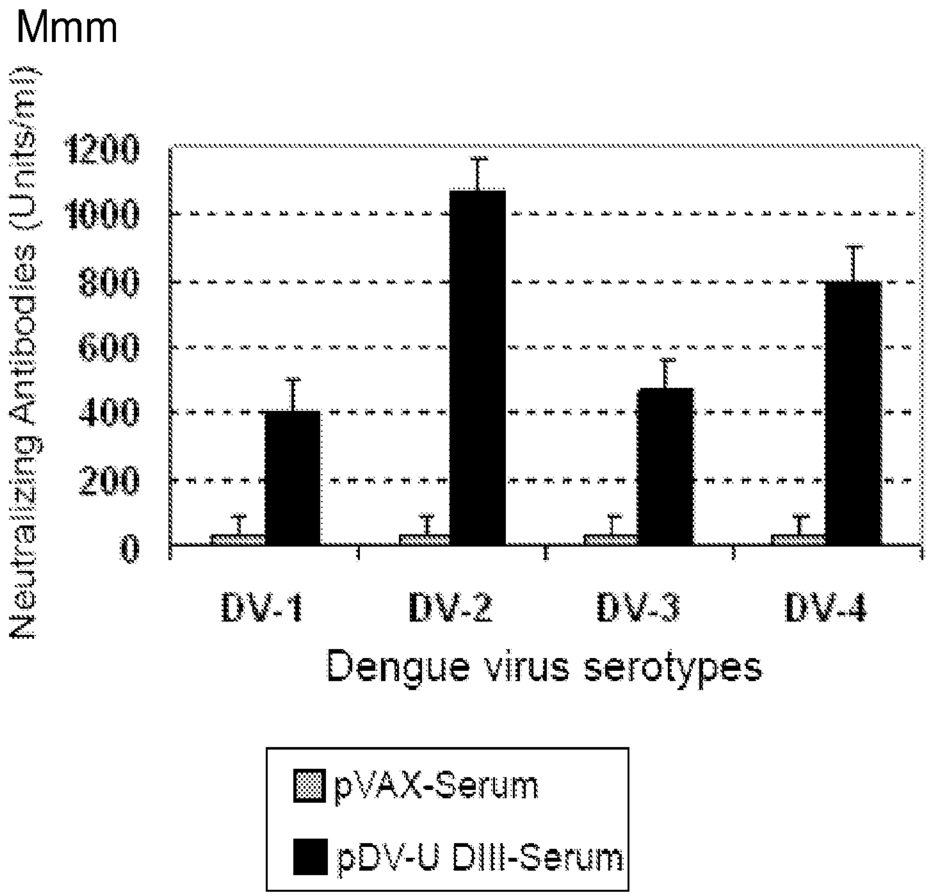
FIG. 16 displays a graph that shows the neutralizing effect of DV-U DIII serum against all four Dengue subtypes.

Further, the neutralizing effect of the pDV-U DIII serum was tested to determine its impact on the cytopathic effects caused by dengue infections. FIG. 16 shows the neutralization data generated (Data from Southern Research Institute, Frederick, Md.) using the DV-U DIII sera with various Dengue-subtypes. This figure indicates that DV-U DIII serum has the ability to neutralize all four Dengue virus subtypes up to the dilution factor of 1:1100. The serum collected from pVAX-vaccinated mice failed to neutralize any of the Dengue virus subtypes.

Example 7

B-cell Activation Against Dengue E DIII Antigens

Mouse spleens of DIII-DNA vaccinated mice were prepared to measure the frequency of B cells capable of producing antibodies directed against DIII proteins.

The Dengue protein suspension was thawed, and the tube was vortexed to suspend to the fine protein particulates. Small aliquots of the resuspended protein were dissolved in Buffer TU (62 mM Tris-HCl/8M urea, pH 8.0) to produce a 10 ug/ml solution. The Dengue proteins were soluble in this buffer. Aliquots of 100 ul (1 ug) of diluted protein were applied to wells of a Pierce HisGrab Copper Coated High Binding Capacity Plate and these antigen coated-Ni-plates were further analysed as per the routine protocols (Yan, J., et al., Enhanced Cellular Immune Responses Elicited by an Engineered HIV-1 Subtype B Consensus-based Envelope DNA Vaccine. Mol. Ther. 15(2): p. 411-421). The same protocol will be applied in future studies involving mice and monkey models. For IFN-gamma ELISPot assays, the 15mer-peptides with 10 overlapping amino acids spanning DIII regions of all four serotypes will be used as antigenic stimulants. These assays will be used from the cells collected from spleens of challenged mice as well as monkey subjects.

Figure 17:
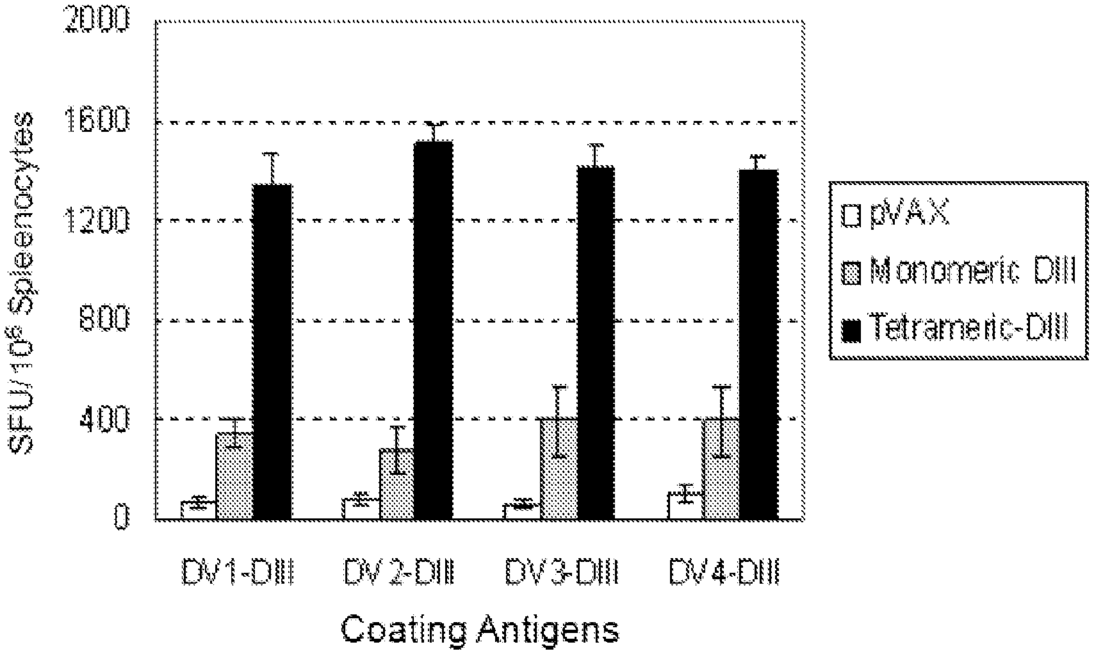
FIG. 17 displays a graph that showing the results of a B cell ELISpot Assay: Induction of anti-DIII antibody secreting cells by pDV-U DIII.

The ELISpot assay results concur with DIII-antibody ELISA data that were described above. Higher frequencies of mouse antibody secreting cells specific for DIII were observed in mice that were vaccinated with pDV-U DIII than the groups that received individual DIII domain alone (FIG. 17). Taken together, the ELISpot results indicated the activation of high-affinity antigen specific B cells that corresponded to the titers of DIII-specific antibodies as determined by ELISA studies.

Example 7

Generation of Dengue Neutralizing Antibody in Rhesus Macaque Monkeys

Macaque monkeys can be vaccinated with pDV-U-DIII Dengue expression construct. After three boosting, the antibody titer can be assessed and the monkeys can be challenged with all four Dengue virus serotypes.

Rhesus macaques are acclimated for 2 months prior to the start of experiments. The study can progress as follows: Week 0—performed 1st immunization (plasmid dose administration) and baseline bleed; Week 2 performed bleed; Week 3 performed 2nd immunization (plasmid dose administration); Week 5 performed bleed; Week 6 performed 3rd immunization (plasmid dose administration) and bleed; Week 8 performed bleed.

The subjects are immunized intramuscularly with pDV-U DIII formulation at a concentration of approximately 1 mg/ml (and preferable about 10 mg/ml) and remaining individual DIII expressing vectors. pVAX can be used as the control vector. Square-wave pulses are to be used in all experiments (Draghia-Akli and Smith, 2003) and delivered with the constant-current CELLECTRA® electroporator (VGX Pharmaceuticals, Blue Bell, Pa.). EP conditions are selected to be the following: 0.5 Amps, 3 pulses, 52 msec, 1 sec between pulses.

What is claimed:

1. A nucleic acid construct capable of expressing a Dengue DIII domain polypeptide that elicits an immune response in a mammal against all four subtypes of Dengue virus, comprising:

an encoding nucleotide sequence that expresses the polypeptide, wherein the polypeptide includes DIII domains from four different Dengue virus subtypes, and a promoter that regulates expression of the polypeptide in the mammal and is operably linked to the encoding nucleotide sequence wherein the encoding nucleotide sequence is selected from the group consisting of SEQ ID NO:1, SEQ ID NO:2, SEQ ID NO:3, SEQ ID NO:4, and SEQ ID NO:5.

* * * * *

SEQUENCE LISTING

<160> NUMBER OF SEQ ID NOS: 18

<210> SEQ ID NO 1

-continued

```
<211> LENGTH: 363
<212> TYPE: DNA
<213> ORGANISM: Dengue virus type 1

<400> SEQUENCE: 1

aagggcacca gctacgtgat gtgcaccggc agcttcaagc tggaaaaaga ggtggccgag      60

actcagcacg gcactgtgct cgtccaggtc aagtacgagg gcaccgacgc cccctgcaag     120

atccccttca gcacccaaga cgagaagggc gtgacacaga acggccggct gatcaccgcc     180

aaccccatcg tgaccgacaa agaaaagccc gtgaacatcg agaccgagcc ccccttcggc     240

gagagctaca tcgtggtggg agccggcgag aaggccctca agctgagttg gttcaaaaag     300

ggcagcagca tcggcaagat gttcgaggcc accgccaggg gcgctcgcag gatggctatt     360

ctc                                                                   363


<210> SEQ ID NO 2
<211> LENGTH: 363
<212> TYPE: DNA
<213> ORGANISM: Dengue virus type 2

<400> SEQUENCE: 2

aagggcatgt cctacagcat gtgtactggc aagttcaagg tcgtcaaaga gatcgccgaa      60

acacaacacg ggaccatcgt gatccgggtg cagtatgagg gcgacggcag cccttgtaag     120

atccctttcg agatcatgga cctggaaaag cggcacgtgc tgggccgcct gatcacagtg     180

aatcctatcg tgacagagaa ggacagccct gtgaatattg aggcagagcc accatttggc     240

gactcctaca tcatcatcgg cgtggagccc ggccagctga agctgaattg gtttaagaag     300

gggtcctcca ttgggcagat gtttgagact actatgagag gcgccaagag aatggctatt     360

ctc                                                                   363


<210> SEQ ID NO 3
<211> LENGTH: 363
<212> TYPE: DNA
<213> ORGANISM: Dengue virus type 3

<400> SEQUENCE: 3

aagggcatga gttacgcaat gtgtctgaac accttcgtgc tgaagaaaga agtgagcgag      60

acacagcatg gcacaatcct gattaaggtg gagtacaagg gcgaggatgc cccttgcaag     120

attccattct ccaccgagga cggccagggc aaggctcaca acggcagact gattacagcc     180

aaccctgtgg tgaccaagaa agaggaacca gtcaatatcg aagccgaacc accattcggc     240

gagtccaaca ttgtgatcgg cattggcgat aaagccctga aaatcaactg gtataagaag     300

ggctcaagca tagggaaaat gtttgaggca actgcccgcg gagcaagaag aatggctatc     360

ttg                                                                   363


<210> SEQ ID NO 4
<211> LENGTH: 363
<212> TYPE: DNA
<213> ORGANISM: Dengue virus type 4

<400> SEQUENCE: 4

aagggcatgt cttacactat gtgctctgga aagttcagca tcgacaaaga gatggctgaa      60

acccagcatg gaaccaccgt ggtgaaggtg aaatatgaag gcgctggggc tccctgtaag     120

gtgcccatcg agatcaggga cgtgaacaaa gaaaaagtgg tgggccggat catcagcagc     180

accccctttcg ccgagaacac caacagcgtg accaacatcg agctggaacc cccctttcggc   240
```

-continued

```
gattcttata tcgtgattgg cgtgggcgac tccgccctga ccctgcactg gttccggaag    300

ggctcctcta taggaaagat gtttgaaagc acctaccggg gagccaaacg catggccatc    360

ctg                                                                  363
```

<210> SEQ ID NO 5
<211> LENGTH: 1515
<212> TYPE: DNA
<213> ORGANISM: Artificial Sequence
<220> FEATURE:
<223> OTHER INFORMATION: Universal Dengue Antigen DNA

<400> SEQUENCE: 5

```
aagggcacca gctacgtgat gtgcaccggc agcttcaagc tggaaaaaga ggtggccgag     60

actcagcacg gcactgtgct cgtccaggtc aagtacgagg gcaccgacgc cccctgcaag    120

atccccttca gcacccaaga cgagaagggc gtgacacaga acggccggct gatcaccgcc    180

aaccccatcg tgaccgacaa agaaaagccc gtgaacatcg agaccgagcc ccccttcggc    240

gagagctaca tcgtggtggg agccggcgag aaggccctca agctgagttg gttcaaaaag    300

ggcagcagca tcggcaagat gttcgaggcc accgccaggg gcgctcgcag gatggctatt    360

ctccggggca ggaagcggcg gagcaagggc atgtcctaca gcatgtgtac tggcaagttc    420

aaggtcgtca aagagatcgc cgaaacacaa cacgggacca tcgtgatccg ggtgcagtat    480

gagggcgacg gcagcccttg taagatccct ttcgagatca tggacctgga aaagcggcac    540

gtgctgggcc gcctgatcac agtgaatcct atcgtgacag agaaggacag ccctgtgaat    600

attgaggcag agccaccatt tggcgactcc tacatcatca tcggcgtgga gcccggccag    660

ctgaagctga attggtttaa gaaggggtcc tccattgggc agatgtttga gactactatg    720

agaggcgcca agagaatggc tattctcaga ggccggaaga gaaggtccaa gggcatgagt    780

tacgcaatgt gtctgaacac cttcgtgctg aagaaagaag tgagcgagac acagcatggc    840

acaatcctga ttaaggtgga gtacaagggc gaggatgccc cttgcaagat tccattctcc    900

accgaggacg gccagggcaa ggctcacaac ggcagactga ttacagccaa ccctgtggtg    960

accaagaaag aggaaccagt caatatcgaa gccgaaccac cattcggcga gtccaacatt   1020

gtgatcggca ttggcgataa agccctgaaa atcaactggt ataagaaggg ctcaagcata   1080

gggaaaatgt ttgaggcaac tgcccgcgga gcaagaagaa tggctatctt gcgtgggaga   1140

aagcgccggt caaagggcat gtcttacact atgtgctctg gaaagttcag catcgacaaa   1200

gagatggctg aaacccagca tggaaccacc gtggtgaagg tgaaatatga aggcgctggg   1260

gctccctgta aggtgcccat cgagatcagg gacgtgaaca aagaaaaagt ggtgggccgg   1320

atcatcagca gcaccccttt cgccgagaac accaacagcg tgaccaacat cgagctggaa   1380

ccccctttcg gcgattctta tatcgtgatt ggcgtgggcg actccgccct gaccctgcac   1440

tggttccgga agggctcctc tataggaaag atgtttgaaa gcacctaccg gggagccaaa   1500

cgcatggcca tcctg                                                    1515
```

<210> SEQ ID NO 6
<211> LENGTH: 121
<212> TYPE: PRT
<213> ORGANISM: Dengue virus type 1

<400> SEQUENCE: 6

```
Lys Gly Thr Ser Tyr Val Met Cys Thr Gly Ser Phe Lys Leu Glu Lys
1               5                   10                  15
```

```
Glu Val Ala Glu Thr Gln His Gly Thr Val Leu Val Gln Val Lys Tyr
            20                  25                  30

Glu Gly Thr Asp Ala Pro Cys Lys Ile Pro Phe Ser Thr Gln Asp Glu
        35                  40                  45

Lys Gly Val Thr Gln Asn Gly Arg Leu Ile Thr Ala Asn Pro Ile Val
    50                  55                  60

Thr Asp Lys Glu Lys Pro Val Asn Ile Glu Thr Glu Pro Pro Phe Gly
65                  70                  75                  80

Glu Ser Tyr Ile Val Val Gly Ala Gly Glu Lys Ala Leu Lys Leu Ser
                85                  90                  95

Trp Phe Lys Lys Gly Ser Ser Ile Gly Lys Met Phe Glu Ala Thr Ala
            100                 105                 110

Arg Gly Ala Arg Arg Met Ala Ile Leu
        115                 120


<210> SEQ ID NO 7
<211> LENGTH: 121
<212> TYPE: PRT
<213> ORGANISM: Dengue virus type 2

<400> SEQUENCE: 7

Lys Gly Met Ser Tyr Ser Met Cys Thr Gly Lys Phe Lys Val Val Lys
1               5                   10                  15

Glu Ile Ala Glu Thr Gln His Gly Thr Ile Val Ile Arg Val Gln Tyr
            20                  25                  30

Glu Gly Asp Gly Ser Pro Cys Lys Ile Pro Phe Glu Ile Met Asp Leu
        35                  40                  45

Glu Lys Arg His Val Leu Gly Arg Leu Ile Thr Val Asn Pro Ile Val
    50                  55                  60

Thr Glu Lys Asp Ser Pro Val Asn Ile Glu Ala Glu Pro Pro Phe Gly
65                  70                  75                  80

Asp Ser Tyr Ile Ile Ile Gly Val Glu Pro Gly Gln Leu Lys Leu Asn
                85                  90                  95

Trp Phe Lys Lys Gly Ser Ser Ile Gly Gln Met Phe Glu Thr Thr Met
            100                 105                 110

Arg Gly Ala Lys Arg Met Ala Ile Leu
        115                 120


<210> SEQ ID NO 8
<211> LENGTH: 121
<212> TYPE: PRT
<213> ORGANISM: Dengue virus type 3

<400> SEQUENCE: 8

Lys Gly Met Ser Tyr Ala Met Cys Leu Asn Thr Phe Val Leu Lys Lys
1               5                   10                  15

Glu Val Ser Glu Thr Gln His Gly Thr Ile Leu Ile Lys Val Glu Tyr
            20                  25                  30

Lys Gly Glu Asp Ala Pro Cys Lys Ile Pro Phe Ser Thr Glu Asp Gly
        35                  40                  45

Gln Gly Lys Ala His Asn Gly Arg Leu Ile Thr Ala Asn Pro Val Val
    50                  55                  60

Thr Lys Lys Glu Glu Pro Val Asn Ile Glu Ala Glu Pro Pro Phe Gly
65                  70                  75                  80

Glu Ser Asn Ile Val Ile Gly Ile Gly Asp Lys Ala Leu Lys Ile Asn
                85                  90                  95
```

```
Trp Tyr Lys Lys Gly Ser Ser Ile Gly Lys Met Phe Glu Ala Thr Ala
            100                 105                 110

Arg Gly Ala Arg Arg Met Ala Ile Leu
        115                 120


<210> SEQ ID NO 9
<211> LENGTH: 121
<212> TYPE: PRT
<213> ORGANISM: Dengue virus type 4

<400> SEQUENCE: 9

Lys Gly Met Ser Tyr Thr Met Cys Ser Gly Lys Phe Ser Ile Asp Lys
1               5                   10                  15

Glu Met Ala Glu Thr Gln His Gly Thr Thr Val Val Lys Val Lys Tyr
            20                  25                  30

Glu Gly Ala Gly Ala Pro Cys Lys Val Pro Ile Glu Ile Arg Asp Val
        35                  40                  45

Asn Lys Glu Lys Val Val Gly Arg Ile Ile Ser Ser Thr Pro Phe Ala
    50                  55                  60

Glu Asn Thr Asn Ser Val Thr Asn Ile Glu Leu Glu Pro Pro Phe Gly
65                  70                  75                  80

Asp Ser Tyr Ile Val Ile Gly Val Gly Asp Ser Ala Leu Thr Leu His
                85                  90                  95

Trp Phe Arg Lys Gly Ser Ser Ile Gly Lys Met Phe Glu Ser Thr Tyr
            100                 105                 110

Arg Gly Ala Lys Arg Met Ala Ile Leu
        115                 120


<210> SEQ ID NO 10
<211> LENGTH: 505
<212> TYPE: PRT
<213> ORGANISM: Artificial Sequence
<220> FEATURE:
<223> OTHER INFORMATION: Universal Dengue Antigen

<400> SEQUENCE: 10

Lys Gly Thr Ser Tyr Val Met Cys Thr Gly Ser Phe Lys Leu Glu Lys
1               5                   10                  15

Glu Val Ala Glu Thr Gln His Gly Thr Val Leu Val Gln Val Lys Tyr
            20                  25                  30

Glu Gly Thr Asp Ala Pro Cys Lys Ile Pro Phe Ser Thr Gln Asp Glu
        35                  40                  45

Lys Gly Val Thr Gln Asn Gly Arg Leu Ile Thr Ala Asn Pro Ile Val
    50                  55                  60

Thr Asp Lys Glu Lys Pro Val Asn Ile Glu Thr Glu Pro Pro Phe Gly
65                  70                  75                  80

Glu Ser Tyr Ile Val Val Gly Ala Gly Glu Lys Ala Leu Lys Leu Ser
                85                  90                  95

Trp Phe Lys Lys Gly Ser Ser Ile Gly Lys Met Phe Glu Ala Thr Ala
            100                 105                 110

Arg Gly Ala Arg Arg Met Ala Ile Leu Arg Gly Arg Lys Arg Arg Ser
        115                 120                 125

Lys Gly Met Ser Tyr Ser Met Cys Thr Gly Lys Phe Lys Val Val Lys
    130                 135                 140

Glu Ile Ala Glu Thr Gln His Gly Thr Ile Val Ile Arg Val Gln Tyr
145                 150                 155                 160
```

-continued

```
Glu Gly Asp Gly Ser Pro Cys Lys Ile Pro Phe Glu Ile Met Asp Leu
            165                 170                 175

Glu Lys Arg His Val Leu Gly Arg Leu Ile Thr Val Asn Pro Ile Val
            180                 185                 190

Thr Glu Lys Asp Ser Pro Val Asn Ile Glu Ala Glu Pro Pro Phe Gly
        195                 200                 205

Asp Ser Tyr Ile Ile Ile Gly Val Glu Pro Gly Gln Leu Lys Leu Asn
    210                 215                 220

Trp Phe Lys Lys Gly Ser Ser Ile Gly Gln Met Phe Glu Thr Thr Met
225                 230                 235                 240

Arg Gly Ala Lys Arg Met Ala Ile Leu Arg Gly Arg Lys Arg Arg Ser
                245                 250                 255

Lys Gly Met Ser Tyr Ala Met Cys Leu Asn Thr Phe Val Leu Lys Lys
            260                 265                 270

Glu Val Ser Glu Thr Gln His Gly Thr Ile Leu Ile Lys Val Glu Tyr
        275                 280                 285

Lys Gly Glu Asp Ala Pro Cys Lys Ile Pro Phe Ser Thr Glu Asp Gly
    290                 295                 300

Gln Gly Lys Ala His Asn Gly Arg Leu Ile Thr Ala Asn Pro Val Val
305                 310                 315                 320

Thr Lys Lys Glu Glu Pro Val Asn Ile Glu Ala Glu Pro Pro Phe Gly
                325                 330                 335

Glu Ser Asn Ile Val Ile Gly Ile Gly Asp Lys Ala Leu Lys Ile Asn
            340                 345                 350

Trp Tyr Lys Lys Gly Ser Ser Ile Gly Lys Met Phe Glu Ala Thr Ala
        355                 360                 365

Arg Gly Ala Arg Arg Met Ala Ile Leu Arg Gly Arg Lys Arg Arg Ser
    370                 375                 380

Lys Gly Met Ser Tyr Thr Met Cys Ser Gly Lys Phe Ser Ile Asp Lys
385                 390                 395                 400

Glu Met Ala Glu Thr Gln His Gly Thr Thr Val Val Lys Val Lys Tyr
                405                 410                 415

Glu Gly Ala Gly Ala Pro Cys Lys Val Pro Ile Glu Ile Arg Asp Val
            420                 425                 430

Asn Lys Glu Lys Val Val Gly Arg Ile Ile Ser Ser Thr Pro Phe Ala
        435                 440                 445

Glu Asn Thr Asn Ser Val Thr Asn Ile Glu Leu Glu Pro Pro Phe Gly
    450                 455                 460

Asp Ser Tyr Ile Val Ile Gly Val Gly Asp Ser Ala Leu Thr Leu His
465                 470                 475                 480

Trp Phe Arg Lys Gly Ser Ser Ile Gly Lys Met Phe Glu Ser Thr Tyr
                485                 490                 495

Arg Gly Ala Lys Arg Met Ala Ile Leu
            500                 505
```

<210> SEQ ID NO 11
<211> LENGTH: 60
<212> TYPE: DNA
<213> ORGANISM: Homo sapiens

<400> SEQUENCE: 11
gccaccatgg actggacctg gatcctgttt ctggtcgctg ctgccactcg ggtgcacagc 60

<210> SEQ ID NO 12
<211> LENGTH: 441

<212> TYPE: DNA
<213> ORGANISM: Artificial Sequence
<220> FEATURE:
<223> OTHER INFORMATION: Dengue Virus 1 Expression Cassette

<400> SEQUENCE: 12
ggtaccgcca ccatggactg gacctggatc ctgtttctgg tcgctgctgc cactcgggtg 60
cacagcaagg gcaccagcta cgtgatgtgc accggcagct tcaagctgga aaaagaggtg 120
gccgagactc agcacggcac tgtgctcgtc caggtcaagt acgagggcac cgacgccccc 180
tgcaagatcc ccttcagcac ccaagacgag aagggcgtga cacagaacgg ccggctgatc 240
accgccaacc ccatcgtgac cgacaaagaa aagcccgtga acatcgagac cgagcccccc 300
ttcggcgaga gctacatcgt ggtgggagcc ggcgagaagg ccctcaagct gagttggttc 360
aaaaagggca gcagcatcgg caagatgttc gaggccaccg ccaggggcgc tcgcaggatg 420
gctattctct gatgactgca g 441

<210> SEQ ID NO 13
<211> LENGTH: 441
<212> TYPE: DNA
<213> ORGANISM: Artificial Sequence
<220> FEATURE:
<223> OTHER INFORMATION: Dengue Virus 2 Expression Cassette

<400> SEQUENCE: 13
ggtaccgcca ccatggactg gacctggatc ctgtttctgg tcgctgctgc cactcgggtg 60
cacagcaagg gcatgtccta cagcatgtgt actggcaagt tcaaggtcgt caaagagatc 120
gccgaaacac aacacgggac catcgtgatc cgggtgcagt atgagggcga cggcagccct 180
tgtaagatcc ctttcgagat catggacctg gaaaagcggc acgtgctggg ccgcctgatc 240
acagtgaatc ctatcgtgac agagaaggac agccctgtga atattgaggc agagccacca 300
tttggcgact cctacatcat catcggcgtg gagcccggcc agctgaagct gaattggttt 360
aagaaggggt cctccattgg gcagatgttt gagactacta tgagaggcgc caagagaatg 420
gctattctct gatgactgca g 441

<210> SEQ ID NO 14
<211> LENGTH: 441
<212> TYPE: DNA
<213> ORGANISM: Artificial Sequence
<220> FEATURE:
<223> OTHER INFORMATION: Dengue Virus 3 Expression Cassette

<400> SEQUENCE: 14
ggtaccgcca ccatggactg gacctggatc ctgtttctgg tcgctgctgc cactcgggtg 60
cacagcaagg gcatgagtta cgcaatgtgt ctgaacacct tcgtgctgaa gaaagaagtg 120
agcgagacac agcatggcac aatcctgatt aaggtggagt acaagggcga ggatgcccct 180
tgcaagattc cattctccac cgaggacggc cagggcaagg ctcacaacgg cagactgatt 240
acagccaacc ctgtggtgac caagaaagag gaaccagtca atatcgaagc cgaaccacca 300
ttcggcgagt ccaacattgt gatcggcatt ggcgataaag ccctgaaaat caactggtat 360
aagaagggct caagcatagg gaaaatgttt gaggcaactg cccgcggagc aagaagaatg 420
gctatcttgt gatgactgca g 441

<210> SEQ ID NO 15
<211> LENGTH: 441
<212> TYPE: DNA

-continued

<213> ORGANISM: Artificial Sequence
<220> FEATURE:
<223> OTHER INFORMATION: Dengue Virus 4 Expression Cassatte

<400> SEQUENCE: 15
ggtaccgcca ccatggactg gacctggatc ctgtttctgg tcgctgctgc cactcgggtg 60
cacagcaagg gcatgtctta cactatgtgc tctggaaagt tcagcatcga caaagagatg 120
gctgaaaccc agcatggaac caccgtggtg aaggtgaaat atgaaggcgc tggggctccc 180
tgtaaggtgc ccatcgagat cagggacgtg aacaaagaaa aagtggtggg ccggatcatc 240
agcagcaccc ctttcgccga gaacaccaac agcgtgacca acatcgagct ggaacccccct 300 ttcggcgatt cttatatcgt gattggcgtg ggcgactccg ccctgaccct gcactggttc 360
cggaagggct cctctatagg aaagatgttt gaaagcacct accggggagc caaacgcatg 420
gccatcctgt gatgactgca g 441

<210> SEQ ID NO 16
<211> LENGTH: 1593
<212> TYPE: DNA
<213> ORGANISM: Artificial Sequence
<220> FEATURE:
<223> OTHER INFORMATION: Universal Dengue Expression Cassette

<400> SEQUENCE: 16
ggtaccgcca ccatggactg gacctggatc ctgtttctgg tcgctgctgc cactcgggtg 60
cacagcaagg gcaccagcta cgtgatgtgc accggcagct tcaagctgga aaaagaggtg 120
gccgagactc agcacggcac tgtgctcgtc caggtcaagt acgagggcac cgacgccccc 180
tgcaagatcc ccttcagcac ccaagacgag aagggcgtga cacagaacgg ccggctgatc 240
accgccaacc ccatcgtgac cgacaaagaa aagcccgtga acatcgagac cgagcccccc 300
ttcggcgaga gctacatcgt ggtgggagcc ggcgagaagg ccctcaagct gagttggttc 360
aaaaagggca gcagcatcgg caagatgttc gaggccaccg ccaggggcgc tcgcaggatg 420
gctattctcc ggggcaggaa gcggcggagc aagggcatgt cctacagcat gtgtactggc 480
aagttcaagg tcgtcaaaga gatcgccgaa acacaacacg ggaccatcgt gatccgggtg 540
cagtatgagg gcgacggcag cccttgtaag atccctttcg agatcatgga cctggaaaag 600
cggcacgtgc tgggccgcct gatcacagtg aatcctatcg tgacagagaa ggacagccct 660
gtgaatattg aggcagagcc accatttggc gactcctaca tcatcatcgg cgtggagccc 720
ggccagctga agctgaattg gtttaagaag gggtcctcca ttgggcagat gtttgagact 780
actatgagag gcgccaagag aatggctatt ctcagaggcc ggaagagaag gtccaagggc 840
atgagttacg caatgtgtct gaacaccttc gtgctgaaga aagaagtgag cgagacacag 900
catggcacaa tcctgattaa ggtggagtac aagggcgagg atgccccttg caagattcca 960
ttctccaccg aggacggcca gggcaaggct cacaacggca gactgattac agccaaccct 1020
gtggtgacca agaaagagga accagtcaat atcgaagccg aaccaccatt cggcgagtcc 1080
aacattgtga tcggcattgg cgataaagcc ctgaaaatca actggtataa gaagggctca 1140
agcataggga aaatgtttga ggcaactgcc cgcggagcaa gaagaatggc tatcttgcgt 1200
gggagaaagc gccggtcaaa gggcatgtct tacactatgt gctctggaaa gttcagcatc 1260
gacaaagaga tggctgaaac ccagcatgga accaccgtgg tgaaggtgaa atatgaaggc 1320
gctggggctc cctgtaaggt gcccatcgag atcagggacg tgaacaaaga aaaagtggtg 1380
ggccggatca tcagcagcac ccctttcgcc gagaacacca acagcgtgac caacatcgag 1440

```
ctggaacccc ctttcggcga ttcttatatc gtgattggcg tgggcgactc cgccctgacc   1500

ctgcactggt tccggaaggg ctcctctata ggaaagatgt ttgaaagcac ctaccgggga   1560

gccaaacgca tggccatcct gtgatgactg cag                                1593


<210> SEQ ID NO 17
<211> LENGTH: 7
<212> TYPE: PRT
<213> ORGANISM: Artificial Sequence
<220> FEATURE:
<223> OTHER INFORMATION: Cleavage sequence

<400> SEQUENCE: 17

Arg Gly Arg Lys Arg Arg Ser
1               5


<210> SEQ ID NO 18
<211> LENGTH: 523
<212> TYPE: PRT
<213> ORGANISM: Artificial Sequence
<220> FEATURE:
<223> OTHER INFORMATION: DV-U DIII Fusion ORF

<400> SEQUENCE: 18

Met Asp Trp Thr Trp Ile Leu Phe Leu Val Ala Ala Ala Thr Arg Val
1               5                   10                  15

His Ser Lys Gly Thr Ser Tyr Val Met Cys Thr Gly Ser Phe Lys Leu
            20                  25                  30

Glu Lys Glu Val Ala Glu Thr Gln His Gly Thr Val Leu Val Gln Val
        35                  40                  45

Lys Tyr Glu Gly Thr Asp Ala Pro Cys Lys Ile Pro Phe Ser Thr Gln
    50                  55                  60

Asp Glu Lys Gly Val Thr Gln Asn Gly Arg Leu Ile Thr Ala Asn Pro
65                  70                  75                  80

Ile Val Thr Asp Lys Glu Lys Pro Val Asn Ile Glu Thr Glu Pro Pro
                85                  90                  95

Phe Gly Glu Ser Tyr Ile Val Val Gly Ala Gly Glu Lys Ala Leu Lys
            100                 105                 110

Leu Ser Trp Phe Lys Lys Gly Ser Ser Ile Gly Lys Met Phe Glu Ala
        115                 120                 125

Thr Ala Arg Gly Ala Arg Arg Met Ala Ile Leu Arg Gly Arg Lys Arg
    130                 135                 140

Arg Ser Lys Gly Met Ser Tyr Ser Met Cys Thr Gly Lys Phe Lys Val
145                 150                 155                 160

Val Lys Glu Ile Ala Glu Thr Gln His Gly Thr Ile Val Ile Arg Val
                165                 170                 175

Gln Tyr Glu Gly Asp Gly Ser Pro Cys Lys Ile Pro Phe Glu Ile Met
            180                 185                 190

Asp Leu Glu Lys Arg His Val Leu Gly Arg Leu Ile Thr Val Asn Pro
        195                 200                 205

Ile Val Thr Glu Lys Asp Ser Pro Val Asn Ile Glu Ala Glu Pro Pro
    210                 215                 220

Phe Gly Asp Ser Tyr Ile Ile Ile Gly Val Glu Pro Gly Gln Leu Lys
225                 230                 235                 240

Leu Asn Trp Phe Lys Lys Gly Ser Ser Ile Gly Gln Met Phe Glu Thr
                245                 250                 255

Thr Met Arg Gly Ala Lys Arg Met Ala Ile Leu Arg Gly Arg Lys Arg
```

-continued

```
            260                 265                 270

Arg Ser Lys Gly Met Ser Tyr Ala Met Cys Leu Asn Thr Phe Val Leu
        275                 280                 285

Lys Lys Glu Val Ser Glu Thr Gln His Gly Thr Ile Leu Ile Lys Val
    290                 295                 300

Glu Tyr Lys Gly Glu Asp Ala Pro Cys Lys Ile Pro Phe Ser Thr Glu
305                 310                 315                 320

Asp Gly Gln Gly Lys Ala His Asn Gly Arg Leu Ile Thr Ala Asn Pro
                325                 330                 335

Val Val Thr Lys Lys Glu Glu Pro Val Asn Ile Glu Ala Glu Pro Pro
            340                 345                 350

Phe Gly Glu Ser Asn Ile Val Ile Gly Ile Gly Asp Lys Ala Leu Lys
        355                 360                 365

Ile Asn Trp Tyr Lys Lys Gly Ser Ser Ile Gly Lys Met Phe Glu Ala
    370                 375                 380

Thr Ala Arg Gly Ala Arg Arg Met Ala Ile Leu Arg Gly Arg Lys Arg
385                 390                 395                 400

Arg Ser Lys Gly Met Ser Tyr Thr Met Cys Ser Gly Lys Phe Ser Ile
                405                 410                 415

Asp Lys Glu Met Ala Glu Thr Gln His Gly Thr Thr Val Val Lys Val
            420                 425                 430

Lys Tyr Glu Gly Ala Gly Ala Pro Cys Lys Val Pro Ile Glu Ile Arg
        435                 440                 445

Asp Val Asn Lys Glu Lys Val Val Gly Arg Ile Ile Ser Ser Thr Pro
    450                 455                 460

Phe Ala Glu Asn Thr Asn Ser Val Thr Asn Ile Glu Leu Glu Pro Pro
465                 470                 475                 480

Phe Gly Asp Ser Tyr Ile Val Ile Gly Val Gly Asp Ser Ala Leu Thr
                485                 490                 495

Leu His Trp Phe Arg Lys Gly Ser Ser Ile Gly Lys Met Phe Glu Ser
            500                 505                 510

Thr Tyr Arg Gly Ala Lys Arg Met Ala Ile Leu
        515                 520
```